(12) United States Patent
Tomizawa

(10) Patent No.: US 10,006,005 B2
(45) Date of Patent: Jun. 26, 2018

(54) CULTURE MEDIUM AND METHOD FOR INDUCING DIFFERENTIATION OF PLURIPOTENT STEM CELLS TO HEPATOBLASTS

(71) Applicant: National University Corporation Chiba University, Chiba (JP)

(72) Inventor: Minoru Tomizawa, Chiba (JP)

(73) Assignee: National University Corporation Chiba University, Chiba (JP)

( * ) Notice: Subject to any disclaimer, the term of this patent is extended or adjusted under 35 U.S.C. 154(b) by 182 days.

(21) Appl. No.: 14/749,715

(22) Filed: Jun. 25, 2015

(65) Prior Publication Data

US 2016/0053230 A1    Feb. 25, 2016

(30) Foreign Application Priority Data

Jun. 27, 2014 (JP) ................. 2014-132167

(51) Int. Cl.
    *C12N 5/00*    (2006.01)
    *C12N 5/071*    (2010.01)

(52) U.S. Cl.
    CPC ........... *C12N 5/067* (2013.01); *C12N 5/0081* (2013.01); *C12N 2500/32* (2013.01); *C12N 2500/34* (2013.01); *C12N 2500/38* (2013.01); *C12N 2501/237* (2013.01); *C12N 2501/48* (2013.01); *C12N 2501/999* (2013.01); *C12N 2506/45* (2013.01)

(58) Field of Classification Search
    None
    See application file for complete search history.

(56) References Cited

U.S. PATENT DOCUMENTS

| | | | | |
|---|---|---|---|---|
| 7,498,171 B2* | 3/2009 | Hariri | ........... | C12N 5/0639 |
| | | | | 435/325 |
| 8,883,504 B2* | 11/2014 | Miyabayashi | ....... | A61K 31/404 |
| | | | | 435/377 |
| 9,732,323 B2* | 8/2017 | Lee | ........... | C12N 5/067 |
| 2005/0153941 A1* | 7/2005 | Miyabayashi | ....... | A61K 31/404 |
| | | | | 514/150 |
| 2013/0259836 A1* | 10/2013 | Lee | ........... | C12N 5/067 |
| | | | | 424/93.7 |

FOREIGN PATENT DOCUMENTS

| | | |
|---|---|---|
| JP | 2005253374 A | 9/2005 |
| JP | 4759723 B2 | 8/2011 |
| JP | 2014128210 A | 7/2014 |

OTHER PUBLICATIONS

Abe et al., "Endoderm-Specific Gene Expression in Embryonic Stem Cells Differentiated to Embryoid Bodies," Experimental Cell Research, vol. 229, No. 1, 1996, pp. 27-34.
Mitaka et al., "Multiple Cell Cycles Occur in Rat Hepatocytes Cultured in the Presence of Nicotinamide and Epidermal Growth Factor," Hepatology, vol. 13, No. 1, 1991, pp. 21-30.
Shan et al., "Identification of small molecules for human hepatocyte expansion and iPS differentiation," Nature Chemical Biology, vol. 9, No. 8, 2013, pp. 514-520.
Tomizawa et al., "Survival of Primary Human Hepatocytes and Death of Induced Pluripotent Stem Cells in Media Lacking Glucose and Arginine," PLoS One, vol. 8, No. 8, e71897, 2013, pp. 1-10.

* cited by examiner

*Primary Examiner* — Blaine Lankford
(74) *Attorney, Agent, or Firm* — Kilyk & Bowersox, P.L.L.C.

(57) ABSTRACT

Provided are a method of inducing differentiation of pluripotent stem cells, such as induced pluripotent stem cells (hereinafter abbreviated as iPS cells), to hepatocytes in a short period of time, and a substance to be used in the method. Specifically, provided are a method of producing a cell culture formed substantially of hepatoblasts, the method including culturing pluripotent stem cells, such as iPS cells, in a culture medium having a composition shown in Table 1 below, and a culture medium for inducing differentiation of pluripotent stem cells into hepatoblasts, which has a composition shown in Table 1 below.

7 Claims, 8 Drawing Sheets

SEQUENCE LISTING

```
<160> NUMBER OF SEQ ID NOS: 60

<210> SEQ ID NO 1
<211> LENGTH: 20
<212> TYPE: DNA
<213> ORGANISM: Artificial
<220> FEATURE:
<223> OTHER INFORMATION: Designed oligonucleotide for use as a primer to
      amplify human Nanog gene

<400> SEQUENCE: 1 ccgttttttgg ctctgttttg                                              20

<210> SEQ ID NO 2
<211> LENGTH: 20
<212> TYPE: DNA
<213> ORGANISM: Artificial
<220> FEATURE:
<223> OTHER INFORMATION: Designed oligonucleotide for use as a primer to
``` amplify human Nanog gene

<400> SEQUENCE: 2
tcatcgaaac actcggtgaa                                                 20

<210> SEQ ID NO 3
<211> LENGTH: 20
<212> TYPE: DNA
<213> ORGANISM: Artificial
<220> FEATURE:
<223> OTHER INFORMATION: Designed oligonucleotide for use as a primer to
      amplify human alpha-fetoprotein gene

<400> SEQUENCE: 3
acacaaaaag cccactccag                                                 20

<210> SEQ ID NO 4
<211> LENGTH: 20
<212> TYPE: DNA
<213> ORGANISM: Artificial
<220> FEATURE:
<223> OTHER INFORMATION: Designed oligonucleotide for use as a primer to
      amplify human alpha-fetoprotein gene

<400> SEQUENCE: 4
ggtgcataca ggaagggatg                                                 20

<210> SEQ ID NO 5
<211> LENGTH: 20
<212> TYPE: DNA
<213> ORGANISM: Artificial
<220> FEATURE:
<223> OTHER INFORMATION: Designed oligonucleotide for use as a primer to
      amplify human ribosomal protein L-19 gene

<400> SEQUENCE: 5
cgaatgccag agaaggtcac                                                 20

<210> SEQ ID NO 6
<211> LENGTH: 20
<212> TYPE: DNA
<213> ORGANISM: Artificial
<220> FEATURE:
<223> OTHER INFORMATION: Designed oligonucleotide for use as a primer to
      amplify human ribosomal protein L-19 gene

<400> SEQUENCE: 6
ccatgagaat ccgcttgttt                                                 20

<210> SEQ ID NO 7
<211> LENGTH: 22
<212> TYPE: DNA
<213> ORGANISM: Artificial
<220> FEATURE:
<223> OTHER INFORMATION: Designed oligonucleotide for use as a primer to
      amplify human albumin gene

<400> SEQUENCE: 7
gctcgtgaaa cacaagccca ag                                              22

<210> SEQ ID NO 8
<211> LENGTH: 23
<212> TYPE: DNA
<213> ORGANISM: Artificial
<220> FEATURE:
<223> OTHER INFORMATION: Designed oligonucleotide for use as a primer to
      amplify human albumin gene

```
<400> SEQUENCE: 8
gcaaagcagg tctccttatc gtc                                          23

<210> SEQ ID NO 9
<211> LENGTH: 24
<212> TYPE: DNA
<213> ORGANISM: Artificial
<220> FEATURE:
<223> OTHER INFORMATION: Designed oligonucleotide for use as a primer to
      amplify human hematopoietically expressed homeobox gene

<400> SEQUENCE: 9
gcccagtgaa cagaataaag gtgc                                         24

<210> SEQ ID NO 10
<211> LENGTH: 22
<212> TYPE: DNA
<213> ORGANISM: Artificial
<220> FEATURE:
<223> OTHER INFORMATION: Designed oligonucleotide for use as a primer to
      amplify human hematopoietically expressed homeobox gene

<400> SEQUENCE: 10
ccaatgccag tggtcatcat cc                                           22

<210> SEQ ID NO 11
<211> LENGTH: 22
<212> TYPE: DNA
<213> ORGANISM: Artificial
<220> FEATURE:
<223> OTHER INFORMATION: Designed oligonucleotide for use as a primer to
      amplify human GATA binding protein 4 gene

<400> SEQUENCE: 11
tctcagtcag tgcgatgtct gg                                           22

<210> SEQ ID NO 12
<211> LENGTH: 23
<212> TYPE: DNA
<213> ORGANISM: Artificial
<220> FEATURE:
<223> OTHER INFORMATION: Designed oligonucleotide for use as a primer to
      amplify human GATA binding protein 4 gene

<400> SEQUENCE: 12
aggagggaag agggaagatt acg                                          23

<210> SEQ ID NO 13
<211> LENGTH: 22
<212> TYPE: DNA
<213> ORGANISM: Artificial
<220> FEATURE:
<223> OTHER INFORMATION: Designed oligonucleotide for use as a primer to
      amplify human CCAAT/enhancer binding protein alpha gene

<400> SEQUENCE: 13
cggacttggt gcgtctaaga tg                                           22

<210> SEQ ID NO 14
<211> LENGTH: 20
<212> TYPE: DNA
<213> ORGANISM: Artificial
<220> FEATURE:
<223> OTHER INFORMATION: Designed oligonucleotide for use as a primer to
      amplify human CCAAT/enhancer binding protein alpha gene
```

```
<400> SEQUENCE: 14
gcattggagc ggtgagtttg                                               20

<210> SEQ ID NO 15
<211> LENGTH: 20
<212> TYPE: DNA
<213> ORGANISM: Artificial
<220> FEATURE:
<223> OTHER INFORMATION: Designed oligonucleotide for use as a primer to
      amplify human Delta like-1 homolog gene

<400> SEQUENCE: 15
ggatgagtgc gtcatagcaa                                               20

<210> SEQ ID NO 16
<211> LENGTH: 20
<212> TYPE: DNA
<213> ORGANISM: Artificial
<220> FEATURE:
<223> OTHER INFORMATION: Designed oligonucleotide for use as a primer to
      amplify human Delta like-1 homolog gene

<400> SEQUENCE: 16
cctcctcttc agcagcattc                                               20

<210> SEQ ID NO 17
<211> LENGTH: 24
<212> TYPE: DNA
<213> ORGANISM: Artificial
<220> FEATURE:
<223> OTHER INFORMATION: Designed oligonucleotide for use as a primer to
      amplify human gamma-glutamyl transpeptidase gene

<400> SEQUENCE: 17
cctcatcctc aacatcctca aagg                                          24

<210> SEQ ID NO 18
<211> LENGTH: 25
<212> TYPE: DNA
<213> ORGANISM: Artificial
<220> FEATURE:
<223> OTHER INFORMATION: Designed oligonucleotide for use as a primer to
      amplify human gamma-glutamyl transpeptidase gene

<400> SEQUENCE: 18
cacctcagtc acatccacaa acttg                                         25

<210> SEQ ID NO 19
<211> LENGTH: 22
<212> TYPE: DNA
<213> ORGANISM: Artificial
<220> FEATURE:
<223> OTHER INFORMATION: Designed oligonucleotide for use as a primer to
      amplify human GATA binding protein 6 gene

<400> SEQUENCE: 19
ccactcgtgt ctgcttttgt gc                                            22

<210> SEQ ID NO 20
<211> LENGTH: 24
<212> TYPE: DNA
<213> ORGANISM: Artificial
<220> FEATURE:
<223> OTHER INFORMATION: Designed oligonucleotide for use as a primer to
      amplify human GATA binding protein 6 gene

<400> SEQUENCE: 20
```
cccttccctt ccatcttctc tcac        24

<210> SEQ ID NO 21
<211> LENGTH: 24
<212> TYPE: DNA
<213> ORGANISM: Artificial
<220> FEATURE:
<223> OTHER INFORMATION: Designed oligonucleotide for use as a primer to
      amplify forkhead box protein A1 gene

<400> SEQUENCE: 21
accccctacg agtttacagg tctg        24

<210> SEQ ID NO 22
<211> LENGTH: 23
<212> TYPE: DNA
<213> ORGANISM: Artificial
<220> FEATURE:
<223> OTHER INFORMATION: Designed oligonucleotide for use as a primer to
      amplify forkhead box protein A1 gene

<400> SEQUENCE: 22
ctgagaagca aatggctctg atg        23

<210> SEQ ID NO 23
<211> LENGTH: 22
<212> TYPE: DNA
<213> ORGANISM: Artificial
<220> FEATURE:
<223> OTHER INFORMATION: Designed oligonucleotide for use as a primer to
      amplify human hepatocyte nuclear factor 1beta gene

<400> SEQUENCE: 23
aaagaacccc agcaaggaag ag        22

<210> SEQ ID NO 24
<211> LENGTH: 22
<212> TYPE: DNA
<213> ORGANISM: Artificial
<220> FEATURE:
<223> OTHER INFORMATION: Designed oligonucleotide for use as a primer to
      amplify human hepatocyte nuclear factor 1beta gene

<400> SEQUENCE: 24
acggacctca gtgaccaagt tg        22

<210> SEQ ID NO 25
<211> LENGTH: 20
<212> TYPE: DNA
<213> ORGANISM: Artificial
<220> FEATURE:
<223> OTHER INFORMATION: Designed oligonucleotide for use as a primer to
      amplify galactokinase-1 gene

<400> SEQUENCE: 25
tgctgtgcct ggggtttatg        20

<210> SEQ ID NO 26
<211> LENGTH: 24
<212> TYPE: DNA
<213> ORGANISM: Artificial
<220> FEATURE:
<223> OTHER INFORMATION: Designed oligonucleotide for use as a primer to
      amplify galactokinase-1 gene

<400> SEQUENCE: 26
gctgcttgag agaggtagaa ggtg                                      24

<210> SEQ ID NO 27
<211> LENGTH: 23
<212> TYPE: DNA
<213> ORGANISM: Artificial
<220> FEATURE:
<223> OTHER INFORMATION: Designed oligonucleotide for use as a primer to
      amplify galactokinase-2 gene

<400> SEQUENCE: 27
tcacgactta ctggagcagg atg                                       23

<210> SEQ ID NO 28
<211> LENGTH: 20
<212> TYPE: DNA
<213> ORGANISM: Artificial
<220> FEATURE:
<223> OTHER INFORMATION: Designed oligonucleotide for use as a primer to
      amplify galactokinase-2 gene

<400> SEQUENCE: 28
caaaaccaaa gccccacctc                                           20

<210> SEQ ID NO 29
<211> LENGTH: 23
<212> TYPE: DNA
<213> ORGANISM: Artificial
<220> FEATURE:
<223> OTHER INFORMATION: Designed oligonucleotide for use as a primer to
      amplify human ornithine transcarbamylase gene

<400> SEQUENCE: 29 ggacatttttt acactgcttg ccc                                      23

<210> SEQ ID NO 30
<211> LENGTH: 24
<212> TYPE: DNA
<213> ORGANISM: Artificial
<220> FEATURE:
<223> OTHER INFORMATION: Designed oligonucleotide for use as a primer to
      amplify human ornithine transcarbamylase gene

<400> SEQUENCE: 30
tccactttct gttttctgcc tctg                                      24

<210> SEQ ID NO 31
<211> LENGTH: 22
<212> TYPE: DNA
<213> ORGANISM: Artificial
<220> FEATURE:
<223> OTHER INFORMATION: Designed oligonucleotide for use as a primer to
      amplify human cytochrome P-450 nifedipine oxidase gene

<400> SEQUENCE: 31
tgagaaatct gaggcgggaa gc                                        22

<210> SEQ ID NO 32
<211> LENGTH: 24
<212> TYPE: DNA
<213> ORGANISM: Artificial
<220> FEATURE:
<223> OTHER INFORMATION: Designed oligonucleotide for use as a primer to
      amplify human cytochrome P-450 nifedipine oxidase gene

<400> SEQUENCE: 32
cgatgttcac tccaaatgat gtgc                                      24

<210> SEQ ID NO 33
<211> LENGTH: 23
<212> TYPE: DNA
<213> ORGANISM: Artificial
<220> FEATURE:
<223> OTHER INFORMATION: Designed oligonucleotide for use as a primer to
      amplify aldehyde dehydrogenase 2 gene

<400> SEQUENCE: 33
gttacttcat ccagcccact gtg                                          23

<210> SEQ ID NO 34
<211> LENGTH: 24
<212> TYPE: DNA
<213> ORGANISM: Artificial
<220> FEATURE:
<223> OTHER INFORMATION: Designed oligonucleotide for use as a primer to
      amplify aldehyde dehydrogenase 2 gene

<400> SEQUENCE: 34
ccaacaacct cctctatggt cttg                                         24

<210> SEQ ID NO 35
<211> LENGTH: 23
<212> TYPE: DNA
<213> ORGANISM: Artificial
<220> FEATURE:
<223> OTHER INFORMATION: Designed oligonucleotide for use as a primer to
      amplify human alpha1-antitrypsin gene

<400> SEQUENCE: 35
ggctgtgctt gatgtatttg agg                                          23

<210> SEQ ID NO 36
<211> LENGTH: 24
<212> TYPE: DNA
<213> ORGANISM: Artificial
<220> FEATURE:
<223> OTHER INFORMATION: Designed oligonucleotide for use as a primer to
      amplify human alpha1-antitrypsin gene

<400> SEQUENCE: 36
gatgttctgg gtgtctgtag ggac                                         24

<210> SEQ ID NO 37
<211> LENGTH: 24
<212> TYPE: DNA
<213> ORGANISM: Artificial
<220> FEATURE:
<223> OTHER INFORMATION: Designed oligonucleotide for use as a primer to
      amplify human tyrosine aminotransferase gene

<400> SEQUENCE: 37
cttggctcct tttgtgtttt cctc                                         24

<210> SEQ ID NO 38
<211> LENGTH: 21
<212> TYPE: DNA
<213> ORGANISM: Artificial
<220> FEATURE:
<223> OTHER INFORMATION: Designed oligonucleotide for use as a primer to
      amplify human tyrosine aminotransferase gene

<400> SEQUENCE: 38
gtccagggca tctttcattg c                                            21

<210> SEQ ID NO 39
<211> LENGTH: 20
<212> TYPE: DNA
<213> ORGANISM: Artificial
<220> FEATURE:
<223> OTHER INFORMATION: Designed oligonucleotide for use as a primer to
      amplify CCAAT/enhancer binding protein beta gene

<400> SEQUENCE: 39
aagcacagcg acgagtacaa                                                20

<210> SEQ ID NO 40
<211> LENGTH: 20
<212> TYPE: DNA
<213> ORGANISM: Artificial
<220> FEATURE:
<223> OTHER INFORMATION: Designed oligonucleotide for use as a primer to
      amplify CCAAT/enhancer binding protein beta gene

<400> SEQUENCE: 40
agctgctcca ccttcttctg                                                20

<210> SEQ ID NO 41
<211> LENGTH: 20
<212> TYPE: DNA
<213> ORGANISM: Artificial
<220> FEATURE:
<223> OTHER INFORMATION: Designed oligonucleotide for use as a primer to
      amplify CCAAT/enhancer binding protein delta gene

<400> SEQUENCE: 41
agaagttggt ggagctgtcg                                                20

<210> SEQ ID NO 42
<211> LENGTH: 20
<212> TYPE: DNA
<213> ORGANISM: Artificial
<220> FEATURE:
<223> OTHER INFORMATION: Designed oligonucleotide for use as a primer to
      amplify CCAAT/enhancer binding protein delta gene

<400> SEQUENCE: 42
cagctgcttg aagaactgcc                                                20

<210> SEQ ID NO 43
<211> LENGTH: 24
<212> TYPE: DNA
<213> ORGANISM: Artificial
<220> FEATURE:
<223> OTHER INFORMATION: Designed oligonucleotide for use as a primer to
      amplify glucose-6-phosphatase gene

<400> SEQUENCE: 43
aacagagcca gtcacagcac caag                                           24

<210> SEQ ID NO 44
<211> LENGTH: 23
<212> TYPE: DNA
<213> ORGANISM: Artificial
<220> FEATURE:
<223> OTHER INFORMATION: Designed oligonucleotide for use as a primer to
      amplify glucose-6-phosphatase gene

<400> SEQUENCE: 44
cctcaggaaa tccattgata cgg                                            23

```
<210> SEQ ID NO 45
<211> LENGTH: 24
<212> TYPE: DNA
<213> ORGANISM: Artificial
<220> FEATURE:
<223> OTHER INFORMATION: Designed oligonucleotide for use as a primer to
      amplify human phosphoenolpyruvate carboxykinase gene

<400> SEQUENCE: 45
ggctacaact tcggcaaata cctg                                              24

<210> SEQ ID NO 46
<211> LENGTH: 24
<212> TYPE: DNA
<213> ORGANISM: Artificial
<220> FEATURE:
<223> OTHER INFORMATION: Designed oligonucleotide for use as a primer to
      amplify human phosphoenolpyruvate carboxykinase gene

<400> SEQUENCE: 46
ttgaacatcc actccagcac cctg                                              24

<210> SEQ ID NO 47
<211> LENGTH: 22
<212> TYPE: DNA
<213> ORGANISM: Artificial
<220> FEATURE:
<223> OTHER INFORMATION: Designed oligonucleotide for use as a primer to
      amplify forkhead box protein A3 gene

<400> SEQUENCE: 47
aaggagatgc cgaaggggta tc                                                22

<210> SEQ ID NO 48
<211> LENGTH: 25
<212> TYPE: DNA
<213> ORGANISM: Artificial
<220> FEATURE:
<223> OTHER INFORMATION: Designed oligonucleotide for use as a primer to
      amplify forkhead box protein A3 gene

<400> SEQUENCE: 48
ctggtagatt tcactcaagg tcagc                                             25

<210> SEQ ID NO 49
<211> LENGTH: 20
<212> TYPE: DNA
<213> ORGANISM: Artificial
<220> FEATURE:
<223> OTHER INFORMATION: Designed oligonucleotide for use as a primer to
      amplify human phenylalanine hydroxylase gene

<400> SEQUENCE: 49
tgtccatgag ctttcacgag                                                   20

<210> SEQ ID NO 50
<211> LENGTH: 20
<212> TYPE: DNA
<213> ORGANISM: Artificial
<220> FEATURE:
<223> OTHER INFORMATION: Designed oligonucleotide for use as a primer to
      amplify human phenylalanine hydroxylase gene

<400> SEQUENCE: 50
ttaaaaccag ggtggtcagc                                                   20

<210> SEQ ID NO 51
```

```
<211> LENGTH: 22
<212> TYPE: DNA
<213> ORGANISM: Artificial
<220> FEATURE:
<223> OTHER INFORMATION: Designed oligonucleotide for use as a primer to
      amplify human hepatocyte nuclear factor 4 alpha, transcript
      variant 2

<400> SEQUENCE: 51
gcaacggaca gatgtgtgag tg                                                   22

<210> SEQ ID NO 52
<211> LENGTH: 22
<212> TYPE: DNA
<213> ORGANISM: Artificial
<220> FEATURE:
<223> OTHER INFORMATION: Designed oligonucleotide for use as a primer to
      amplify human hepatocyte nuclear factor 4 alpha, transcript
      variant 2

<400> SEQUENCE: 52
agagaggggc ttgacgattg tg                                                   22

<210> SEQ ID NO 53
<211> LENGTH: 20
<212> TYPE: DNA
<213> ORGANISM: Artificial
<220> FEATURE:
<223> OTHER INFORMATION: Designed oligonucleotide for use as a primer to
      amplify human sex determining region Y-box7 gene

<400> SEQUENCE: 53
actccactcc aacctccaag                                                      20

<210> SEQ ID NO 54
<211> LENGTH: 20
<212> TYPE: DNA
<213> ORGANISM: Artificial
<220> FEATURE:
<223> OTHER INFORMATION: Designed oligonucleotide for use as a primer to
      amplify human sex determining region Y-box7 gene

<400> SEQUENCE: 54
gtggccagga gtgttcaaat                                                      20

<210> SEQ ID NO 55
<211> LENGTH: 20
<212> TYPE: DNA
<213> ORGANISM: Artificial
<220> FEATURE:
<223> OTHER INFORMATION: Designed oligonucleotide for use as a primer to
      amplify human hepatocyte nuclear factor 1 alpha gene

<400> SEQUENCE: 55
acctgtccca acacctcaac                                                      20

<210> SEQ ID NO 56
<211> LENGTH: 20
<212> TYPE: DNA
<213> ORGANISM: Artificial
<220> FEATURE:
<223> OTHER INFORMATION: Designed oligonucleotide for use as a primer to
      amplify human hepatocyte nuclear factor 1 alpha gene

<400> SEQUENCE: 56
ctcatcacct gtgggctctt                                                      20
```

```
<210> SEQ ID NO 57
<211> LENGTH: 20
<212> TYPE: DNA
<213> ORGANISM: Artificial
<220> FEATURE:
<223> OTHER INFORMATION: Designed oligonucleotide for use as a primer to
      amplify human forkhead box protein A2 gene

<400> SEQUENCE: 57
gatacctcct actaccaggg                                                 20

<210> SEQ ID NO 58
<211> LENGTH: 20
<212> TYPE: DNA
<213> ORGANISM: Artificial
<220> FEATURE:
<223> OTHER INFORMATION: Designed oligonucleotide for use as a primer to
      amplify human forkhead box protein A2 gene

<400> SEQUENCE: 58
cacttgctct ctcacttgtc                                                 20

<210> SEQ ID NO 59
<211> LENGTH: 19
<212> TYPE: DNA
<213> ORGANISM: Artificial
<220> FEATURE:
<223> OTHER INFORMATION: Designed oligonucleotide for use as a primer to
      amplify human hepatocyte nuclear factor 4 gamma gene

<400> SEQUENCE: 59
tcagtcattt cacaccagc                                                  19

<210> SEQ ID NO 60
<211> LENGTH: 19
<212> TYPE: DNA
<213> ORGANISM: Artificial
<220> FEATURE:
<223> OTHER INFORMATION: Designed oligonucleotide for use as a primer to
      amplify human hepatocyte nuclear factor 4 gamma gene

<400> SEQUENCE: 60
tgccaaaagt gctatcctg                                                  19
```

CULTURE MEDIUM AND METHOD FOR INDUCING DIFFERENTIATION OF PLURIPOTENT STEM CELLS TO HEPATOBLASTS

TECHNICAL FIELD

The present invention relates to a culture medium and a method for inducing differentiation of pluripotent stem cells into hepatoblasts. More specifically, the present invention relates to a culture medium and a method for inducing differentiation of induced pluripotent stem cells into hepatoblasts.

BACKGROUND ART

Pluripotent stem cells are cells having both a self-renewal ability to renew themselves and pluripotency. In recent years, a transplantation therapy using cells differentiated from pluripotent stem cells has attracted attention in regenerative medicine aimed at regeneration and functional recovery of cells, tissues, and organs with malfunction or dysfunction. In addition, the cells differentiated from pluripotent stem cells are expected to be applied to, for example, drug toxicity tests. As described above, it is a big issue in a pharmaceutical field to induce differentiation of pluripotent stem cells into cells of interest and amplify the cells of interest.

Induced pluripotent stem cells (hereinafter sometimes abbreviated as iPS cells) and embryonic stem cells (hereinafter sometimes abbreviated as ES cells) are known as pluripotent stem cells. Those cells are each expected to be applied to, for example, regenerative medicine based on a transplantation therapy or the like involving inducing differentiation into cells of interest and using the cells of interest, and drug toxicity tests.

For example, when hepatocytes can be induced to differentiate from human iPS cells or human ES cells, it is expected to develop a transplantation therapy to the cases of liver failure. Liver is constructed mainly of hepatocytes which are hepatic parenchymal cells, hepatic nonparenchymal cells such as bile duct epithelial cells, and the like. The liver is an organ which secretes bile, filters and detoxifies absorbed nutrients, metabolizes drugs, stores sugars, and regulates blood glucose, and besides, produces fibrinogen, heparin, an anti-anemic substance, and the like, and thus is an organ essential for life. Therefore, liver failure, in which the number of functioning hepatocytes excessively decreases, is a fatal pathological condition. In the cases of liver failure, there occurs an extremely severe condition such as bleeding tendency due to an excessive lack of coagulation factors, or hepatic coma. Transplantation of the hepatocytes can serve as a radical therapy for such pathological condition.

The inventor of the present invention provided a method to induce differentiation of ES cells into hepatocytes and obtain a cell culture product substantially composed of hepatocytes from a cell group containing the differentiated hepatocytes (Japanese Patent No. 4759723 and Japanese Patent Application Laid-open No. 2005-253374). Specifically, the inventor focused attention on the fact that the hepatocytes had a series of enzymes involved in glycolysis, a urea cycle, and the like, and hence survived in a medium containing galactose and ornithine that were added as substrates, but not containing glucose and arginine that were produced by the series of enzymes, and provided a method of producing a cell culture product substantially composed of hepatocytes through culture of cells differentiated from ES cells in such medium in which cells differentiated into other cells than hepatocytes died.

However, application of human ES cells to humans involves immune rejection due to the fact that the ES cells are embryonic stem cells derived from others, and an ethical problem.

Meanwhile, iPS cells, which are pluripotent stem cells induced from somatic cells such as human fibroblasts by a gene recombinant technology, are capable of being produced from autologous cells. Thus, the iPS cells hardly cause a problem such as immune rejection, and are expected to be applied to regenerative medicine (Takahashi, K. et al., "Induction of Pluripotent Stem Cells from Adult Human Fibroblasts by Defined Factors," Cell, 2007, Vol. 131, No. 5, p. 861-872).

As a technology for inducing differentiation of human iPS cells into hepatocytes, there is a report on, for example, a method in which growth factors and/or transcription factors for promoting differentiation to hepatocytes were each added and introduced to culture of human iPS cells (Tomizawa, M. et al., "Liver", 2011, Vol. 52, (Suppl. 2): A680, Inamura et al., "Efficient Generation of Hepatoblasts from Human ES Cells and iPS Cells by Transient Overexpression of Homeobox Gene HEX," Molecular Therapy, 2011, Vol. 19, No. 2, p. 400-407, and Tomizawa, M. et al., "Single-step protocol for the differentiation of human-induced pluripotent stem cells into hepatic progenitor-like cells," Biomedical Reports, 2013, Vol. 1, p. 18-22 (published online on Monday, Aug. 13, 2012 as Doi: 10.3892/br.2012.2)).

There is also a report on a method of forming liver from human iPS cells (Takebé, T. et al., "Vascularized and functional human liver from a iPSC-derived organ bud transplantation," Nature, 2013, Vol. 499, p. 481-489). This method is a method of forming liver, comprising firstly promoting differentiation from iPS cells into hepatocytes in vitro, mixing the resultant with vascular endothelial cells and mesenchymal stem cells, and then transplanting the mixture into a mouse brain. Such a method is required to have no exposure to foreign proteins when applied to humans. In addition, the iPS cells that were promoted to differentiate into hepatocytes die when they are not transplanted into the mouse brain, but are maintained in vitro. Further, it takes several weeks to induce differentiation to hepatocytes in vitro by such method, and besides, mature hepatocytes cannot be obtained (Si-Tayeb, K. et al., "Highly efficient generation of human hepatocyte-like cells from induced pluripotent stem cells," Hepatology, 2010, Vol. 51, p. 297-305). Accordingly, in order to achieve the application to humans, it is essential to develop a method of producing hepatocytes from iPS cells in a short period of time without any exposure to foreign proteins.

As described above, the iPS cells are expected to be applied to regenerative medicine. However, when inducing differentiation of iPS cells into cells of interest in vitro, the resultant obtained is a cell group containing undifferentiated iPS cells as well as the cells of interest, and hence there is a risk in that the remaining undifferentiated iPS cells form a tumor through transplantation (Cunningham et al., "Lessons from human teratomas to guide development of safe stem cell therapies," Nature Biotechnology, 2012, Vol. 30, p. 849-8.57). Accordingly, it is necessary to separate differentiation-induced cells from a cell group containing the differentiation-induced cells and undifferentiated iPS cells, in order to utilize cells induced to differentiate from iPS cells in regenerative medicine, such as transplantation.

The inventor of the present invention developed and reported a method of collecting only human primary cultured hepatocytes from co-culture of human iPS cells with human primary cultured hepatocytes by killing the human iPS cells, and hepatocyte selection medium (HSM) to be used in the method (Tomizawa, M. et al., "Survival of primary human hepatocytes and death of induced pluripotent stem cells in media lacking glucose and arginine," PLoS One, 2013, Vol. 8, e71897 and Japanese Patent Application No. 2012-286978). This medium is prepared by adding galactose and ornithine, but not adding glucose and arginine that are essential for cell survival. The hepatocytes have a series of enzymes involved in gluconeogenesis and a urea cycle, and hence can synthesize glucose and arginine. Thus, the hepatocytes can survive even when cultured in HSM. However, the human iPS cells lack gluconeogenesis and the urea cycle, and die in 3 days when cultured in HSM. Therefore, when a method of producing hepatocytes from human iPS cells is established, the remaining undifferentiated human iPS cells can be removed from a produced cell group by culturing the cell group in HSM for 3 days, and a cell culture consisting substantially of hepatocytes can be obtained. HSM is constructed only of ingredients contained in a general medium, and thereby has an extremely low risk of damaging the resultant hepatocytes.

CITATION LIST

Patent Literature

[PTL 1] Japanese Patent No. 4759723
[PTL 2] Japanese Patent Application Laid-open No. 2005-253374
[PTL 3] Japanese Patent Application No. 2012-286978
[PTL 4] Japanese Patent Application Laid-open No. 2012-143229

Non Patent Literature

[NPL 1] Takahashi, K. et al., "Induction of Pluripotent Stem Cells from Adult Human Fibroblasts by Defined Factors," Cell, 2007, Vol. 131, No. 5, p. 861-872.
[NFL 2] Tomizawa, M. et al., "Liver", 2011, Vol. 52, (Suppl. 2): A680.
[NFL 3] Inamura et al., "Efficient Generation of Hepatoblasts from Human ES Cells and iPS Cells by Transient Overexpression of Homeobox Gene HEX," Molecular Therapy, 2011, Vol. 19, No. 2, p. 400-407.
[NPL 4] Tomizawa, M. et al., "Single-step protocol for the differentiation of human-induced pluripotent stem cells into hepatic progenitor-like cells," Biomedical Reports, 2013, Vol. 1, p. 18-22 (published online on Monday, Aug. 13, 2012 as Doi: 10.3892/br.2012.2).
[NPL 5] Takebe, T. et al., "Vascularized and functional human liver from a iPSC-derived organ bud transplantation," Nature, 2013, Vol. 499, p. 481-48.
[NFL 6] Si-Tayeb, K. et al., "Highly efficient generation of human hepatocyte-like cells from induced pluripotent stem cells," Hepatology, 2010, Vol. 51, p. 297-305.
[NFL 7] Cunningham et al., "Lessons from human teratomas to guide development of safe stem cell therapies," Nature Biotechnology, 2012, Vol. 30, p. 849-857.
[NPL 8] Tomizawa, M. et al., "Survival of primary human hepatocytes and death of induced pluripotent stem cells in media lacking glucose and arginine," PLoS One, 2013, Vol. 8, e71897
[NPL 9] Tomizawa, M. et al., "Activin A is essential for feeder-free culture of human induced pluripotent stem cells," Journal of Cellular Biochemistry (in press), (published online as DOI:10.1002/jcb.24395).
[NPL 10] Kakinuma, S. et al., "Analyses of cell surface molecules on hepatic stem/progenitor cells in mouse fetal liver," Journal of Hepatology, 2009, Vol. 51, No. 1, p. 127-138.
[NPL 11] Sangan, C. B. et al., "Hepatic progenitor cells", Cell and Tissue Research, 2010, Vol. 342, No. 2, p. 131-137.
[NPL 12] Mitaka, T. et al., "Multiple cell cycles occur in rat hepatocytes cultured in the presence of nicotinamide and epidermal growth factor," Hepatology, 1991, Vol. 13, No. 1, p. 21-30.
[NPL 13] Abe, K. et al., "Endoderm-specific gene expression in embryonic stem cells differentiated to embryoid bodies," Experimental Cell Research, 1996, Vol. 229, No. 1, p. 27-34.
[NPL 14] Shan, J. et al., "Identification of small molecules for human hepatocyte expansion and iPS differentiation," Nature Chemical Biology, 2013, Vol. 9, No. 8, p. 514-520.

SUMMARY OF INVENTION

Technical Problem

An object of the present invention is to provide a method of inducing differentiation of human iPS cells into hepatocytes in a short period of time, and a substance to be used in the method.

Solution to Problem

The inventor of the present invention made extensive investigations in order to achieve the object. As a result, the inventor found a culture medium capable of inducing differentiation of iPS cells into hepatoblasts by culturing the iPS cells for 2 days in the culture medium. The inventor also found that when a cell group containing both hepatoblasts induced to differentiate from iPS cells and undifferentiated iPS cells is cultured by using the culture medium, a cell culture product substantially composed of hepatoblasts is obtained separately from the cell group. The present invention was achieved based on such findings.

That is, the present invention relates to a method of producing hepatoblasts from pluripotent stem cells, the method comprising culturing pluripotent stem cells in a culture medium having a composition shown in Table 1 below.

TABLE 1

| HDI (1 L) | inorganic salts | |
|---|---|---|
| | $CaCl_2,2H_2O$ | 0.185 g |
| | $MgCl_2,6H_2O$ | 0.203 g |
| | $MgSO_4$ (anhyd) | 0.098 g |
| | KCl | 0.4 g |
| | $KH_2PO_4$ | 0.06 g |
| | NaCl | 7.915 g |
| | $Na_2HPO_4$ | 0.19 g |
| | amino acids | |
| | L-alanine | 0.225 g |
| | L-asparagine,$H_2O$ | 0.25 g |
| | L-cysteine | 0.12 g |
| | glycine | 0.2 g |
| | L-histidine,HCl,$H_2O$ | 0.25 g |
| | L-isoleucine | 0.25 g |

TABLE 1-continued

| | |
|---|---|
| L-leucine | 0.125 g |
| L-lysine,HCl | 0.075 g |
| L-methionine | 0.075 g |
| L-phenylalanine | 0.125 g |
| L-serine | 0.2 g |
| L-threonine | 0.3 g |
| L-tryptophan | 0.02 g |
| L-valine | 0.1 g |
| Others | |
| phenol red, Na | 0.01 g |
| NaHCO$_3$ | 2.745 g |
| MEM vitamin solution (100 X) | 10 ml |
| knockout serum replacement | 100 ml |
| glutamine | 0.3 g |
| ornithine | 0.169 g |
| galactose | 0.9 g |
| oncostatin M | 0.02 g |
| FPH1 | 3.88 g |
| M50054 | 100 mg |
| non-essential amino acids | 10 ml |
| sodium pyruvate | 10 ml |
| nicotinamide | 1.2 g |
| proline | 0.03 g |

The present invention also relates to the above-mentioned method of producing hepatoblasts from pluripotent stem cells, the method further comprising, before culturing pluripotent stem cells in the culture medium having a composition shown in Table 1 above, culturing the pluripotent stem cells in any one of culture media selected from the group consisting of the following culture media:
(1) Leibovitz's-15;
(2) William's E medium; and
(3) Dulbecco's Modified Eagle Medium: Nutrient Mixture F-12.

The present invention further relates to any one of the above-mentioned methods, in which the pluripotent stem cells is iPS cells.

The present invention still further relates to any one of the above-mentioned methods, in which the culturing pluripotent stem cells in a culture medium having a composition shown in Table 1 is culturing the pluripotent stem cells in the culture medium for at least 2 days.

The present invention still further relates to any one of the above-mentioned methods, in which the culturing pluripotent stem cells in a culture medium having a composition shown in Table 1 is culturing the pluripotent stem cells in the culture medium for 2 days.

The present invention also relates to a method of producing hepatoblasts from iPS cells, the method comprising culturing iPS cells in a culture medium having a composition shown in Table 1 above for 2 days.

The present invention also relates to a method of producing hepatoblasts from iPS cells, the method comprising:
(A) culturing iPS cells in any one of culture media selected from the group consisting of the following culture media for 7 days:
(1) Leibovitz's-15;
(2) William's E medium; and
(3) Dulbecco's Modified Eagle Medium: Nutrient Mixture F-12; and
(B) culturing cells obtained in the step (A) in a culture medium having a composition shown in Table 1 above for 2 days.

The present invention also relates to a culture medium for inducing differentiation of pluripotent stem cells into hepatoblasts, which has a composition shown in Table 1 above.

The present invention also relates to a cell culture product, which is produced by any one of the above-mentioned methods.

Advantages of the Invention

According to embodiments of the present invention, provided are the culture medium and the method for inducing differentiation of pluripotent stem cells, such as iPS cells, into hepatoblasts. The culture medium according to the embodiment of the present invention is capable of inducing differentiation of iPS cells into hepatoblasts by culturing the iPS cells for 2 days in the culture medium.

In the resultant cultured cells, the expressions of α-fetoprotein (hereinafter sometimes abbreviated as AFP) and delta like-1 homolog (hereinafter sometimes abbreviated as DLK-1), both of which are markers of hepatoblasts, were found to be upregulated. In addition, cytochrome P-450 nifedipine oxidase (sometimes abbreviated as CYP3A4), an enzyme involved in drug metabolism, and aldehyde dehydrogenase 2 (sometimes abbreviated as ALDH2), an enzyme involved in alcohol metabolism, were increased to levels comparable to those in fetal liver. Accordingly, it is expected that the hepatoblasts obtained by such culture may be used in, for example, in vitro tests on a drug metabolism function and an alcohol metabolism function of hepatocytes, and drug toxicity tests.

On the other hand, the expression of Nanog in such cultured cells was reduced to a level comparable to that in fetal liver, suggesting that the cells had lost pluripotency. Accordingly, the hepatoblasts obtained by such culture are, considered to have an extremely low risk of forming a tumor when transplanted for liver disease treatment, and hence are highly useful.

As described above, according to the embodiment of the present invention, the cell culture product containing the hepatoblasts induced to differentiate from the iPS cells can be provided.

BRIEF DESCRIPTION OF THE DRAWINGS

In FIG. 1, FF means ReproFF used as a control medium (Example 1).

In FIG. 3, FF means ReproFF used as a control medium (Example 1).

In FIG. 4, FF means ReproFF used as a control medium, (-) means no addition of growth factors, Act means activin A, FGF means basic fibroblast growth factor, NFG means β-nerve growth factor, Dex means dexamethasone, ITS means insulin-transferrin-sodium-selenite media supplement, EGF means epidermal growth factor, TGF means transforming growth factor, BMP means bone morphogenetic protein-4, RA means all trans retinoic acid, OnM means oncostatin M, and HGF means hepatocyte growth factor. The panel B shows the relative expression level of AFP in cultured cells after 48 hours of culture of iPS cells in HSM supplemented with oncostatin M or hepatocyte growth factor. In FIG. 4, Fetal means fetal liver (Example 1).

In FIG. 5, FT means ReproFF used as a control medium (Example 1).

In FIG. 6, AFP means α-fetoprotein, DLK-1 means delta like-1 homolog, G-GTP means γ-glutamyl transpeptidase, A1-AT means al-antitrypsin, TAT means tyrosine aminotransferase, FF means ReproFF used as a control medium, Fetal means fetal liver, and Adult means adult liver (Example 1).

In FIG. 7, CEBPA means CCAAT/enhancer binding protein α, CEBPB means CCAAT/enhancer binding protein β, CEBPD means CCAAT/enhancer binding protein δ, HNF4G means hepatocyte nuclear factor 4γ, HNF4A means hepatocyte nuclear factor 4α, transcript variant 2, FoxA3 means forkhead box protein A3, FoxA2 means forkhead box protein A2, HNF1A means hepatocyte nuclear factor 1α, Sox7 means sex determining region Y-box7, FoxA1 means forkhead box protein A1, GATA6 means GATA binding protein 6, HNF1B means hepatocyte nuclear factor 1β, HEX means hematopoietically expressed homeobox, GATA4 means GATA binding protein 4, FF means ReproFF used as a control medium, Fetal means fetal liver, and Adult means adult liver (Example 1).

DETAILED DESCRIPTION OF THE INVENTION

Figure 1:
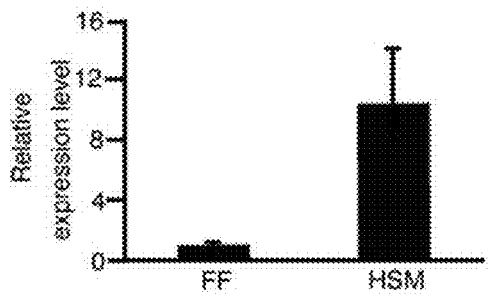
FIG. 1 shows that the expression of AFP, a marker of fetal hepatocytes, was upregulated in a cell culture product obtained by culturing a human iPS cell line (201B7) in HSM for 2 days. The ordinate axis of FIG. 1 indicates a relative expression level.

The present invention relates to a culture medium and a method for inducing differentiation of pluripotent stem cells into hepatoblasts. The term "culture medium" is hereinafter sometimes referred to simply as medium. More specifically, the present invention relates to a culture medium and a method for inducing differentiation of induced pluripotent stem cells into hepatoblasts. The present invention also relates to a cell culture produced by the method according to the present invention.

The culture medium according to the present invention is a culture medium prepared by adding oncostatin M, hepatocyte functional proliferation inducer 1 (FPH1), M50054, non-essential amino acids, sodium pyruvate, nicotinamide, and L-glutamine to hepatocyte selection medium (HSM; Tomizawa, M. et al., "Survival of primary human hepatocytes and death of induced pluripotent stem cells in media lacking glucose and arginine," PLoS One, 2013, Vol. 8, e71897 and Japanese Patent Application No. 2012-286978). Herein, the culture medium according to the present application is referred to as hepatocyte differentiation inducer, which is sometimes abbreviated as HDI.

HDI is preferably supplemented with serum or a serum replacement, preferably a serum replacement before use. Any serum may be used as long as the serum is generally used for the culture of pluripotent stem cells, hepatoblasts, and hepatocytes. When the serum is used, it is preferred to use serum derived from a living organism of the same species as the species of cells to be cultured. For example, when the cells to be cultured are human cells, it is preferred to use human-derived serum. The serum replacement is a substance to be used for the maintenance and growth of cells in place of the serum, and means a composition having a known chemical composition. Any serum replacement may be used as long as the serum replacement is generally used for the culture of pluripotent stem cells, hepatoblasts, and hepatocytes. Examples thereof may include Knockout™ Serum Replacement (manufactured by Life Technologies), CDM-HD Serum Replacement (manufactured by FiberCell Systems), StemSure Serum Replacement (manufactured by Wako Pure Chemical Industries, Ltd.), and Nu-Serum™ (manufactured by Becton Dickinson). The dose of the serum or the serum replacement may be determined by simple repeated experiments.

HDI may be specifically exemplified by a medium having a composition shown in Table 1 below. HDI may be a medium having a composition in which insulin, dexamethasone, and aprotinin are added to the composition shown in Table 1. The presence or absence of the addition of insulin, dexamethasone, and aprotinin to a medium has substantially no influence on an inducing effect on differentiation of iPS cells into hepatoblasts. Insulin may be added so that its final concentration is from $10^{-8}$ M to $10^{-10}$ M, preferably from $10^{-9}$ M to $10^{-10}$ M, more preferably $10^{-9}$ M. Dexamethasone may be added so that its final concentration is from $10^{-8}$ M to $10^{-10}$ M, preferably from $10^{-9}$ M to $10^{-10}$ M, more preferably $10^{-9}$ M. Aprotinin may be added so that its final concentration is from 10 U/mL to 300 U/mL, preferably from 30 U/mL to 200 U/mL, more preferably from 50 U/mL to 100 U/mL, still more preferably 50 U/mL. The addition concentrations of insulin, dexamethasone, and aprotinin are not limited to those exemplified concentrations, and may each be any concentration as long as differentiation of induced pluripotent stem cells into hepatoblasts can be induced. The addition concentrations may each be easily determined by simple repeated experiments.

TABLE 1

| HDI (1 L) | | |
|---|---|---|
| inorganic salts | | |
| $CaCl_2,2H_2O$ | 0.185 | g |
| $MgCl_2,6H_2O$ | 0.203 | g |
| $MgSO_4$(anhyd) | 0.098 | g |
| KCl | 0.4 | g |
| $KH_2PO_4$ | 0.06 | g |
| NaCl | 7.915 | g |
| $Na_2HPO_4$ | 0.19 | g |
| amino acids | | |
| L-alanine | 0.225 | g |
| L-asparagine,$H_2O$ | 0.25 | g |
| L-cysteine | 0.12 | g |
| glycine | 0.2 | g |
| L-histidine,HCl,$H_2O$ | 0.25 | g |
| L-isoleucine | 0.25 | g |
| L-leucine | 0.125 | g |
| L-lysine,HCl | 0.075 | g |
| L-methionine | 0.075 | g |
| L-phenylalanine | 0.125 | g |
| L-serine | 0.2 | g |
| L-threonine | 0.3 | g |
| L-tryptophan | 0.02 | g |
| L-valine | 0.1 | g |
| Others | | |
| phenol red, Na | 0.01 | g |
| $NaHCO_3$ | 2.745 | g |
| MEM vitamin solution (100 X) | 10 | ml |
| knockout serum replacement | 100 | ml |
| glutamine | 0.3 | g |
| ornithine | 0.169 | g |
| galactose | 0.9 | g |
| oncostatin M | 0.02 | g |
| FPH1 | 3.88 | g |
| M50054 | 100 | mg |
| non-essential amino acids | 10 | ml |
| sodium pyruvate | 10 | ml |
| nicotinamide | 1.2 | g |
| proline | 0.03 | g |

In the medium having a composition shown in Table 1, the concentrations of constituents of MEM vitamin solution in terms of final concentration are as follows: 0.085 g of sodium chloride; 0.001 g of choline chloride; 0.001 g of folic acid; 0.001 g of myo-inositol; 0.001 g of niacinamide; 0.001 g of D-pantothenic acid.1/2Ca; 0.001 g of pyridoxal.HCl; 0.0001 g of riboflavin; and 0.001 g of thiamine.HCl.

The pluripotent stem cells refer to stem cells having a self-renewal ability for a long period of time under predetermined culture conditions, and having pluripotency to many kinds of cells under predetermined differentiation inducing conditions. Any cells may be used as the pluripotent stem cells as long as the cells have both a self-renewal ability to renew themselves and pluripotency. Specific examples thereof may include iPS cells and ES cells. Of those, iPS cells are preferably recommended.

The iPS cells are pluripotent stem cells that are induced from somatic cells such as human fibroblasts by a genetic recombination technology. The iPS cells may be derived from any species as long as the cells are produced from somatic cells of mammals, such as humans and mice. However, when the iPS cells are used in regenerative medicine such as transplantation, it is preferred to use iPS cells produced from somatic cells derived from species that is same as that of a subject of the regenerative medicine. It is more preferred to use iPS cells produced from somatic cells collected from an individual of the subject.

The iPS cells may be prepared by any method to be generally used (e.g., Takahashi, K. et al., "Induction of Pluripotent Stem Cells from Adult Human Fibroblasts by Defined Factors," Cell, 2007, Vol. 131, No. 5, p. 861-872.). In addition, the iPS cells may be passaged by using a known method for maintaining and culturing the cells in an undifferentiated state (Japanese Patent Application Laid-open No. 2012-143229 and Tomizawa, M. et al., "Activin A is essential for feeder-free culture of human induced pluripotent stem cells," Journal of Cellular Biochemistry (in press), (published online as DOI: 10.1002/jcb.24395)).

The hepatoblasts, which are tissue stem cells derived from foregut endoderm, are essential for liver tissue development. The hepatoblasts are supposed to be tissue stem cells in fetal liver, and are present in an extremely small number in mature liver. The hepatoblasts present in mature liver are considered to be activated in association with liver damage and play an important role in liver repair. It has been reported that many transcription factors, and various extracellular matrices that are produced by nonparenchymal cells, such as hepatocyte growth factor (HGF) and transforming growth factor β (TGF-β), are involved in differentiation of hepatoblasts to hepatocytes. The hepatoblasts can be cultured in vitro, and can differentiate to hepatic parenchymal cells or bile duct epithelial cells by culturing under appropriate culture conditions.

The hepatocytes as used herein are meant to include cells at all differentiation stages which are determined to differentiate to hepatocytes, such as hepatic progenitor cells and mature hepatocytes. The mature hepatocytes, which are also called mature hepatic parenchymal cells, are terminally differentiated cells expressing a wide variety of liver-specific functions, for example, functions such as a cholesterol synthesis ability, amino acid transport activity, and glucose-6-phosphatase activity. Meanwhile, the mature hepatocytes have an active proliferative ability, which is well known in the phenomenon of liver regeneration. There are a report that the hepatic progenitor cells are cells having an ability to actively proliferate and differentiate to hepatocytes and bile duct epithelium, which are found at the fetal stage (Kakinuma, S. et al., "Analyses of cell surface molecules on hepatic stem/progenitor cells in mouse fetal liver," Journal of Hepatology, 2009, Vol. 51, No. 1, p. 127-138) and a report that the hepatic progenitor cells are small and oval cells which are generated in liver regeneration process (Sangan, C. B. et al., "Hepatic progenitor cells", Cell and Tissue Research, 2010, Vol. 342, No. 2, p. 131-137). Thus, the hepatic progenitor cells have a proliferation ability and an ability to differentiate to hepatocytes and bile duct epithelial cells. The hepatic progenitor cells have a higher proliferation ability than the mature hepatocytes, and also form bile duct epithelium. Therefore, when the hepatic progenitor cells are transplanted into liver, the cells rapidly forms the existing construction of liver. Thus, it can be expected to regenerate lost liver more effectively than the transplantation of hepatocytes only (Sangan, C. B. et al., "Hepatic progenitor cells", Cell and Tissue Research, 2010, Vol. 342, No. 2, p. 131-137).

Herein, the cells that are determined to differentiate from pluripotent stem cells to hepatocytes are sometimes referred to as hepatocyte-lineage cells. The hepatocyte-lineage cells encompass cells at various stages of a differentiation process from pluripotent stem cells to hepatocytes, ranging from cells in the initial stage of the differentiation process to mature hepatocytes.

The method according to the present invention has a feature of culturing pluripotent stem cells in HDI. A period of time for which the pluripotent stem cells are cultured in HDI is preferably at least 2 days or more, more preferably from 2 days to 7 days, still more preferably from 2 days to 4 days, yet still more preferably 2 days. As culture conditions, there may be used any of general culture conditions, preferably known conditions which have been used in the culture of pluripotent stem cells and in culture for inducing differentiation of pluripotent stem cells into hepatoblasts or hepatocytes. Specific examples thereof may include culture conditions to be performed at from 35° C. to 40° C., preferably 37° C. under the atmosphere of 95% air and 5% $CO_2$. It is appropriate that medium exchange be performed once every preferably from 1 day to 2 days, more preferably 2 days.

In addition, the method according to the present invention may be a method comprising preculturing pluripotent stem cells in a culture medium other than HDI, changing the culture media to HDI, and then further culturing the cells in HDI for at least 2 days or more, preferably from 2 days to 7 days, still more preferably from 2 days to 4 days, yet still more preferably 2 days. Examples of the culture medium used in the preculture may include Leibovitz's-15, William's E medium, and Dulbecco's Modified Eagle Medium: Nutrient Mixture F-12. A more preferred example thereof may be Leibovitz's-15. Those culture media are each preferably supplemented with serum or a serum replacement, preferably a serum replacement before use. In addition, those culture media may each be supplemented with an effective amount of a compound or a reagent having an effect on the growth of desired cells, such as proline or nicotinamide, before use. A period of time for the preculture is preferably at least 2 days or more, more preferably 7 days. As culture conditions for the preculture, there may be used any of general culture conditions, preferably known conditions which have been used in the culture of pluripotent stem cells and in culture for inducing differentiation of pluripotent stem cells into hepatoblasts or hepatocytes. Specific examples thereof may include culture conditions to be performed at from 35° C. to 40° C., preferably 37° C. under the atmosphere of 95% air and 5% $CO_2$. A cell survival rate is increased in the case where the pluripotent stem cells are precultured in a culture medium other than HDI and then cultured in HDI as compared to the case where the pluripotent stem cells are not precultured, which results in an increase in number of hepatoblasts obtained. In the method according to the present invention, it is more preferred that the pluripotent stem cells be precultured in a culture medium other than HDI and then cultured in HDI.

The induction of differentiation of iPS cells into hepatoblasts or hepatocytes by the method according to the present invention may be confirmed by detecting the expression of a known marker of hepatoblasts or hepatocytes. Examples of such marker may include AFP and DLK-1, markers of hepatoblasts, and enzymes characteristically expressed in hepatocytes. Such enzymes include CYP3A4 that is involved in drug metabolism, and ALDH2 that is involved in alcohol metabolism. In addition, an example of the marker of hepatocytes may be albumin.

The detection of the marker of hepatoblasts or hepatocytes may be performed by reverse transcribing mRNA of a target protein in the cells, followed by measuring the mRNA by a known genetic engineering technique, such as a polymerase chain reaction (PCR), a reverse transcriptase polymerase chain reaction (RT-PCR), or a real-time quantitative polymerase chain reaction. The detection of the marker may also be performed using an antibody against a target protein by enzyme-linked immunoassay (ELISA method) or an immunostaining method. However, the detection is not limited to those methods, and any of known methods may be used.

The expression of Nanog, which is specifically expressed in pluripotent stem cells and early embryo, almost disappears in the cultured cells obtained by the method according to the present invention, which suggests that the cells had lost pluripotency. Accordingly, such cultured cells are considered to have an extremely low risk of forming a tumor when used in transplantation for treatment of liver disease.

The cell culture product obtained by the method of the present invention is a cell culture product containing hepatoblasts. The "cell culture product" refers to a cell group obtained after culturing cells. The cell culture product of the present invention is substantially free of cells having pluripotency. The "substantially free" refers to that the ratio of the cell number of hepatoblasts to the cell number of cells having pluripotency (the cell number of hepatoblasts:the cell number of cells having pluripotency) is 1,000:1 or less, preferably 10,000:1 or less, more preferably 100,000:1 or less. In addition, the cell culture product of the present invention may contain, in addition to the hepatoblasts, cells further differentiated from the hepatoblasts.

The cell culture product obtained by the method according to the present invention may be used as, for example, a drug in regenerative medicine including transplantation treatment for a liver disease, such as fulminant hepatitis, or liver failure occurring after partial hepatectomy or in the natural course of liver cirrhosis. A drug containing, as an active ingredient, the cell culture product obtained by the method of the present invention may contain physiological saline, an additive, a medium, or the like which is pharmacologically acceptable, and is preferably not contaminated with impurities, such as foreign serum and a virus.

In addition, the cell culture product obtained by the method of the present invention can be made to differentiate to hepatic parenchymal cells and bile duct epithelial cells by culturing in vitro under appropriate culture conditions. For example, it has been reported that many transcription factors, and various extracellular matrices produced by non-parenchymal cells, such as HGF and TGF-β, are involved in differentiation of hepatoblasts to hepatocytes. The induction of differentiation of hepatoblasts to hepatocytes may be carried out in vitro through the utilization of those substances. As described above, the cell culture product obtained by the culture medium and the method according to the present invention may be used for obtaining hepatic parenchymal cells or bile duct epithelial cells by further inducing differentiation using a known method.

Further, the cell culture product obtained by the method of the present invention may be utilized in, for example, in vitro tests on a drug metabolism function and an alcohol metabolism function of hepatocytes, and drug toxicity tests on hepatocytes.

The present invention is further described in more detail below by way of Examples. However, the scope of the present invention is not limited to the following Examples.

Example 1

Studies were performed to search for a substance and a medium each exhibiting an inducing effect on differentiation of human iPS cells into hepatoblasts or hepatocytes through culture in a short period of time. Specifically, a substance having an inducing effect on differentiation into hepatoblasts or hepatocytes was selected by adding a test substance in the culture of human iPS cells and then detecting the expression of a hepatocyte-specific gene in the cultured cells.

1. Cell Culture

A human iPS cell line (201B7; Riken Cell Bank) was seeded to a 25-cm$^2$ flask (manufactured by Asahi Glass Co., Ltd.), a 6-well plate (manufactured by Asahi Glass Co., Ltd.), or a 96-well flat-bottomed plate (manufactured by Asahi Glass Co., Ltd.), which is coated with Matrigel, and was cultured in a 5% $CO_2$ incubator at 37° C. The coating with Matrigel was performed by: adding a solution prepared by adding 8.7 ml of Dalbecco's Modified Eagle's Medium/Nutrient F-12 Ham (manufactured by Sigma) to 0.3 ml of Matrigel™ (manufactured by Becton Dickinson) to a 25-cm$^2$ flask, a 6-well plate, and a 96-well flat-bottomed plate, in amounts of 1 ml, 0.5 ml, and 20 µl, respectively; and leaving the whole to stand still at room temperature for 30 minutes. ReproFF (manufactured by ReproCELL Incorporated) was used as a cell culture medium. ReproFF is a culture medium for culturing primate ES cells or human IFS cells while maintaining the pluripotency. The cells were passaged by culture using a 25-cm$^2$ flask. The cells were dispersed as described below. After the aspiration of the medium, the 25-cm$^2$ flask was rinsed with 1 ml of physiological saline per flask. After the aspiration of the saline, 0.5 ml of Accutase (manufactured by Innovative Cell Technologies) was added and the cells were incubated in an incubator for 5 minutes. 0.5 ml of ReproFF was added, and the cells were harvested. Then, the cells were centrifuged at 1,000 rpm for 3 minutes. The supernatant was removed by aspiration, and then the precipitated cells were used by being suspended in ReproFF.

A medium used in a search study on various growth factors (hereinafter abbreviated as iPSm[-]) was prepared by adding 20% Knockout™ Serum Replacement (hereinafter abbreviated as KSR; manufactured by Life Technologies), Minimum Essential Amino Acids (manufactured by Life Technologies), 2 mM L-glutamine (manufactured by Life Technologies), and 1 mM 2-mercaptoethanol (manufactured by Sigma-Aldrich) to Dulbecco's Minimum Essential Medium-F12 (manufactured by Sigma-Aldrich) (Takahashi, K. et al., "Induction of Pluripotent Stem Cells from Adult Human Fibroblasts by Defined Factors," Cell, 2007, Vol. 131, No. 5, p. 861-872).

An optical microscope CKX41N-31PHP (manufactured by Olympus Corporation) was used for an optical microscopic observation of cells.

cell observation with an optical microscope.

2. Real-Time Quantitative PCR

Cell differentiation was confirmed by measuring an expression gene by real-time quantitative PCR. RNA was extracted by using Isogen (manufactured by NIPPON GENE) according to the manufacturer's instructions. 5 µg of total RNA was synthesized by using Superscript3 first-strand synthesis system for PCR (manufactured by Life Technologies) and an oligo dT primer according to the manufacturer's instructions. Real-time quantitative PCR was performed using 4 ng of synthesized cDNA per sample. The primers used are shown in Table 2. PCR was performed as follows: PCR were 40 cycles of denaturation for 5 seconds and annealing-extension for 5 seconds. SYBR Green Master Mix (manufactured by Life Technologies) was used for the reaction. Mini Opticon system (manufactured by Bio-Rad) was used for detection in real-time PCR. The expression level of each gene was calculated as an average value of data obtained from three wells. Ribosomal protein L (RPL)-19 was used as an internal control and the expression level of each gene was represented as a relative expression level to the expression level of RPL-19.

TABLE 2

| primer | | | | amplified gene | | |
|---|---|---|---|---|---|---|
| name | | sequence | SEQ ID NO. | name | GenBank accession number | product size |
| OMC311 | forward | CCGTTTTTGGCTCTGTTTTG | 1 | hNanog | NM_024865 | 187 bp |
| OMC312 | reverse | TCATCGAAACACTCGGTTGAA | 2 | hNanog | | |
| OMC317 | forward | ACACAAAAAGCCCACTCCAG | 3 | hAFP | NM_001134 | 147 bp |
| OMC318 | reverse | GCTGCATACAGGAAGGGATG | 4 | hAFP | | |
| OMC321 | forward | CGAATGCCAGAGAAGGTCAC | 5 | hRPL19 | BC000530 | 157 bp |
| OMC322 | reverse | CCATGAGAATCCGCTTGTTT | 6 | hRPL19 | | |
| OMC329 | forward | GCTCGTGAAACACAAGCCCAAG | 7 | hAlbumin | NM_000477 | 114 bp |
| OMC330 | reverse | GCAAAGCAGGTCTCCTTATCGTC | 8 | hAlbumin | | |
| OMC347 | forward | GCCCAGTGAACAGAATAAAGGTGC | 9 | hHEX | NM_002729 | 167 bp |
| OMC348 | reverse | CCAATGCCAGTGGTCATCATCC | 10 | hHEX | | |
| OMC349 | forward | TCTCAGTCAGTGCGATGTCTGG | 11 | hGATA4 | NM_002052 | 197 bp |
| OMC350 | reverse | AGGAGGGAAGAGGGAAGATTACG | 12 | hGATA4 | | |
| OMC351 | forward | CGGACTTGGTGCGTCTAAGATG | 13 | hCEBPA | U34070 | 148 bp |
| OMC352 | reverse | GCATTGGAGCGGTGAGTTTG | 14 | hCEBPA | | |
| OMC367 | forward | GGATGAGTGCGTCATAGCAA | 15 | hDk-1 | NM_005618 | 121 bp |
| OMC368 | reverse | CCTCCTCTTCAGCAGCATTC | 16 | hDk-1 | | |
| OMC385 | forward | CCTCATCCTCAACATCCTCAAAGG | 17 | hG-GTP | J04131 | 163 bp |
| OMC386 | reverse | CACCTCAGTCACATCCACAAACTTG | 18 | hG-GTP | | |
| OMC387 | forward | CCACTCGTGTCTGCTTTTGTGC | 19 | hGATA6 | NM_005257 | 139 bp |
| OMC388 | reverse | CCCTTCCCTTCCATCTTCTCTCAC | 20 | hGATA6 | | |
| OMC429 | forward | ACCCCCTACGAGTTTACAGGTCTG | 21 | FoxA1 | BC033890 | 166 bp |
| OMC430 | reverse | CTGAGAAGCAAATGGCTCTGATG | 22 | FoxA1 | | |
| OMC499 | forward | AAAGAACCCCAGCAAGGAAGAG | 23 | hHNF1B | BC017714 | 170 bp |
| OMC500 | reverse | ACGGACCTCAGTGACCAAGTTG | 24 | hHNF1B | | |
| OMC511 | forward | TGCTGTGCCTGGGGTTTATG | 25 | GALK1 | NM_003154 | 153 bp |
| OMC512 | reverse | GCTGCTTGAGAGAGGTAGAAGGTG | 26 | GALK1 | | |
| OMC513 | forward | TCACGACTTACTGGAGCAGGATG | 27 | GALK2V1 | NM_002044 | 177 bp |
| OMC514 | reverse | CAAAACCAAAGCCCCACCTC | 28 | hGALK2V1 | | |
| OMC515 | forward | GGACATTTTTACACTGCTTGCCC | 29 | hOTC | BC107153 | 105 bp |
| OMC516 | reverse | TCCACTTTCTGTTTTCTGCCTCTG | 30 | hOTC | | |
| OMC527 | forward | TGAGAAATCTGAGGCGGGAAGC | 31 | hCYP3A4 | J04449 | 111 bp |
| OMC528 | reverse | CGATGTTCACTCCAAATGATGTGC | 32 | hCYP3A4 | | |
| OMC537 | forward | GTTACTTCATCCAGCCCACTGTG | 33 | ALDH2 | AY621070 | 121 bp |
| OMC538 | reverse | CCAACAACCTCCTCTATGGTCTTG | 34 | hALDH2 | | |
| OMC549 | forward | GGCTGTGCTTGATGTATTTGAGG | 35 | hA1-AT | NM_001085 | 154 bp |
| OMC550 | reverse | GATGTTCTGGGTGTCTGTAGGGAC | 36 | hA1-AT | | |
| OMC551 | forward | CTTGGCTCCTTTTGTGTTTTCCTC | 37 | hTAT | BC020707 | 105 bp |

TABLE 2-continued

| primer | | | amplified gene | | |
|---|---|---|---|---|---|
| name | | sequence | SEQ ID NO. | name | GenBank accession number | product size |
| OMC552 | reverse | GTCCAGGGCATCTTTCATTGC | 38 | hTAT | | |
| OMC569 | forward | AAGCACAGCGACGAGTACAA | 39 | CEBPB | BC007538 | 155 bp |
| OMC570 | reverse | AGCTGCTCCACCTTCTTCTG | 40 | CEBPB | | |
| OMC571 | forward | AGAAGTTGGTGGAGCTGTCG | 41 | CEBPD | BC105109 | 101 bp |
| OMC572 | reverse | AGCTGCTTGAAGAACTGCC | 42 | CEBPD | | |
| OMC579 | forward | AACAGAGCCAGTCACAGCACCAAG | 43 | G6P | NM_000151 | 139 bp |
| OMC580 | reverse | CCTCAGGAAATCCATTGATACGG | 44 | G6P | | |
| OMC581 | forwards | GGCTACAACTTCGGCAAATACCTG | 45 | hPEPCK | NM_002591 | 167 bpp |
| OMC582 | reverse | TTGAACATCCACTCCAGCACCCTG | 48 | hPEPCK | | |
| OMC587 | forward | AAGGAGATGCCGAAGGGGTATC | 47 | FoxA3 | BC016024 | 129 bp |
| OMC588 | reverse | CTGGTAGATTTCACTCAAGGTCAGC | 48 | FoxA3 | | |
| OMC591 | forward | TGTCCATGAGCTTTCACGAG | 49 | hPAH | NM_000277 | 135 bp |
| OMC592 | reverse | TTAAAACCAGGGTGGTCAGC | 50 | hPAH | | |
| OMC611 | forward | GCAACGGACAGATCTGTGAGTG | 51 | hHNF4Av2 | NM_000457 | 146 bp |
| OMC612 | reverse | AGAGAGGGGCTTGACGATTGIG | 52 | hHNF4Av2 | | |
| OMC615 | forward | ACTCCACTCCAACCTCCAAG | 53 | hSox7 | NM_031439 | 151 bp |
| OMC616 | reverse | GTGGCCAGGAGTGTTCAAAT | 84 | hSox7 | | |
| OMC631 | forward | ACCTGTCCCAACACCTCAAC | 55 | hHNF1A | M57732 | 152 bp |
| OMC632 | reverse | CTCATCACCTGTGCGCTCTT | 56 | hHNF1A | | |
| OMC689 | forward | GATACCTCCTACTACCAGGG | 57 | hFoxA2 | NM_021784 | 121 bp |
| OMC690 | reverse | CACTTGCTCTCTCACTTGTC | 58 | hFoxA2 | | |
| OMC695 | forward | TCAGTCATTTCACACCAGC | 59 | hHNF4G | BC105011 | 126 bp |
| OMC696 | reverse | TGCCAAAAGTGCTATCCTG | 60 | hHNF4G | | |

3. Cell Proliferation Assay

A human iPS cell line (201B7, Riken Cell Bank) was seeded to a 96-well flat-bottomed plate coated with Matrigel at 1,000 cells/50 μl per well. After 48 hours of culture, 3-(4,5-dimethylthiazol-2-yl)-5-(3-carboxymethoxyphenyl)-2-(4-sulfophenyl)-2H-tetrazolium inner salt (MTS; manufactured by Promega) was added at 5 μl per well, and the cells were incubated in an incubator for 2 hours. After that, cell proliferation was verified by measuring an absorbance at a wavelength of 490 nm with iMark™ Microplate Absorbance Reader (manufactured by Bio-Rad).

4. Reagents

Reagents used in Examples and compounds to be investigated are listed below.

100×NEAA (manufactured by Life Technologies). The composition of 100×NEAA is as follows: glycine 750.0 mg/L; L-alanine 890.0 mg/L; L-asparagine 1,320.0 mg/L; L-aspartic acid 1,330.0 mg/L; L-glutamic acid 1,470.0 mg/L; L-proline 1,150.0 mg/L; and L-serine 1,050.0 mg/L.

100× sodium pyruvate (manufactured by Life Technologies). Sodium pyruvate provides an energy source and a carbon skeleton for a process of anabolic action through its addition to a culture medium. Sodium pyruvate is added in culture under special conditions, such as culture in a serum-free medium or a reduced serum medium, or culture for cloning.

A CTP inhibitor, 4-chloro-3-[[(3-nitrophenyl)amino]sulfonyl]-benzoic acid, was used which was commercially available from Sigma.

M50054 (2,2'-methylenebis(1,3-cyclohexanedione)) was used, which was known as an apoptosis inhibitor and was commercially available from Merck.

A DAPK inhibitor, (4Z)-4-(3-pyridylmethylene)-2-styryl-oxazol-5-one, was used which was commercially available from Merck.

Oncostatin M (hereinafter sometimes abbreviated as OnM; manufactured by Wako Pure Chemical Industries, Ltd.). Oncostatin M is a cytokine of the IL-6 family which plays important functions in hematopoiesis, immunity, metabolism, and the like.

Hepatocyte growth factor (hereinafter abbreviated as HGF) was used, which was commercially available from Wako Pure Chemical Industries, Ltd.

Hepatocyte functional proliferation inducer 1 (hereinafter abbreviated as FPH1), 2-(N-(5-chloro-2-methylphenyl)methylsulfonamido)-N-(2,6-difluorophenyl)acetamide, was used which was commercially available from Xcess Biosciences, Inc.

Hepatocyte functional enhancer 1 (hereinafter abbreviated as FH1), N,N'-(methylenebis(4,1-phenylene))diacetamide, was used which was commercially available from Xcess Biosciences, Inc.

Activin A (hereinafter sometimes abbreviated as Act) was used, which was commercially available from R&D Systems, Inc. Activin A is a cytokine belonging to the transforming growth factor-$\beta$ (TGF-$\beta$) superfamily produced by a large number of cell species in a developmental process, and is known to be involved in cell proliferation and differentiation.

Basic fibroblast growth factor (hereinafter sometimes abbreviated as FGF) was used, which was commercially available from Wako Pure Chemical Industries, Ltd. FGF is known as a growth factor involved in angiogenesis and embryogenesis.

$\beta$-nerve growth factor (hereinafter sometimes abbreviated as NGF) was used, which was commercially available from R&D Systems, Inc. NGF is known to have actions such as neurite elongation, neuron maintenance, the repair of cell damage, and the recovery of a cranial nerve function.

Dexamethasone (hereinafter sometimes abbreviated as Dex) was used, which was commercially available from Wako Pure Chemical Industries, Ltd. Dex is used as a steroidal anti-inflammatory agent, and is known to be involved in cell adhesion and maintenance in the primary monolayer culture of hepatocytes or the like through its addition to a medium.

Insulin-transferrin-sodium-selenite media supplement (hereinafter abbreviated as ITS) was used which was commercially available from Sigma. The commercially available 100× solution was diluted 100-fold before use in culture. The composition of 100× ITS is as follows: 1.0 mg/mL human insulin; 0.55 mg/mL human transferrin (containing no iron); and 0.5 µg/mL sodium selenite.

Epidermal growth factor (hereinafter sometimes abbreviated as EGF) was used, which was commercially available from Wako Pure Chemical Industries, Ltd. EGF is known to be involved in the proliferation and differentiation of a wide range of cell types derived from ectoderm and mesoderm.

Transforming growth factor-1 (hereinafter sometimes abbreviated as TGF) was used, which was commercially available from R&D Systems, Inc. TGF is a cytokine involved in signaling related to histogenesis and cell division.

Bone morphogenic protein-4 (hereinafter abbreviated as BMP-4) was used, which was commercially available from Wako Pure Chemical Industries, Ltd. BMP-4 is a protein belonging to the TGF-$\beta$ superfamily, and is known to be involved in a developmental process, such as the induction of a tissue or an organ at a developmental stage, pattern formation, the induction of cell death, and the control of cell differentiation.

All trans retinoic acid (hereinafter sometimes abbreviated as RA) was used, which was commercially available from Sigma was used as RA is known to be involved in cell differentiation and proliferation.

Human fetal liver-derived total RNA A was used, which was commercially available from Clontech Human adult liver-derived total RNA A was used, which was commercially available from Clontech.

5. Preparation of Hepatocyte Differentiation Inducer

HDI was prepared by adding 20 ng/mL oncostatin M, 10 nM FPH1, and 100 µg/mL M50054 to hepatocyte selection medium (HSM; Tomizawa, M. et al., "Survival of primary human hepatocytes and death of induced pluripotent stem cells in media lacking glucose and arginine," PLoS One, 2013, Vol. 8, e71897 and Japanese Patent Application No. 2012-286978) and further adding 100×NEAA and 100× sodium pyruvate so as to make each concentration to 1/100 through dilution. Nicotinamide (manufactured by Wako Pure Chemical Industries, Ltd.) and L-glutamine (manufactured by Wako Pure Chemical Industries, Ltd.) were added at concentrations of 1.2 mg/mL and 0.3 mg/mL, respectively. Nicotinamide is essential for the cell division of primary hepatocytes (Mitaka, T. et al., "Multiple cell cycles occur in rat hepatocytes cultured in the presence of nicotinamide and epidermal growth factor," Hepatology, 1991, Vol. 13, No. 1, p. 21-30).

The composition of HDI is shown in Table 1 above. In addition, the composition of HSM is shown in Table 3.

TABLE 3

| | | | |
|---|---|---|---|
| L1S-ES medium (1 L) | inorganic salts | | |
| | CaCl$_2$,2H$_2$O | 1M solution | 1.258 ml |
| | MgCl$_2$,6H$_2$O | | 0.203 |
| | MgSO$_4$ (anhyd) | | 0.098 g |
| | KCl | 1M solution | 5.3655 ml |
| | KH$_2$PO$_4$ | | 0.06 |
| | NaCl | 5M solution | 27.29 ml |
| | | | (7.915 g) |
| | Na$_2$HPO$_4$,2H$_2$O | | 0.14014 g |
| | amino acids | | |
| | L-alanine | | 0.225 g |
| | L-arginine,HCl | | 0 |
| | L-asparagine,H$_2$O | | 0.25 g |
| | L-cysteine | | 0.12 g |
| | L-cystine,2HCl | | 0 g |
| | L-glutamine | | 0.3 g |
| | glycine | | 0.2 g |
| | L-histidine,HCl,H$_2$O | | 0.25 g |
| | L-isoleucine | | 0.25 g |
| | L-leucine | | 0.125 g |
| | L-lysine,HCl | | 0.075 g |
| | L-methionine | | 0.075 g |
| | L-phenylalanine | | 0.125 g |
| | L-serine | | 0.2 g |
| | L-threonine | | 0.3 g |
| | L-tryptophan | | 0.02 g |
| | L-valine | | 0.1 g |
| | L-ornithine,HCl | | 0.169 g |
| Gibco MEM vitamin (100 X dilution) | vitamins | | |
| | NaCl | | 0.085 g |
| | choline chloride | | 0.001 g |
| | folate | | 0.001 g |
| 10 ml | myo-inositol | | 0.001 g |
| | nyacinamide | | 0.001 g |
| | D-pantothenic acid,1/2Ca | | 0.001 g |
| | pyridoxal,HCl | | 0.001 g |
| | riboflavin | | 0.0001 g |
| | thiamine,HCl | | 0.001 g |
| Others | Others | | |
| | C(+)galactose | | 0.9 g |
| | D-glucose | | 0 g |
| | phenol red, Na | | 0.01 g |
| | glycerol (specific gravity 1.26 g/ml) | | 0.365 ml |
| | sodium pyruvate | | 0 ml |
| | proline | | 0.03 g |
| | 7.5% sodium bicarbonate solution | | 36.6 ml |
| | mercaptoethanol | | 1000 µl |
| | non-essential amino acids | | 0 |

6. Results

First, iPS cells were cultured in HSM to confirm differentiation of the iPS cells to hepatocytes. Specifically, iPS cells were cultured in HSM for 2 days, and then gene expression in the cells was measured by real-time quantitative PCR. Thus, the induction of differentiation of iPS cells to hepatocytes was detected. ReproFF was used as a control medium and similar investigations were performed.

As shown in FIG. 1, the expression of AFP gene, a marker of fetal hepatocytes, was found to be upregulated when the iPS cells were cultured in HSM. On the other hand, the gene was expressed at a low level when the iPS cells were cultured in ReproFF. This suggested that as disclosed in the previous report (Tomizawa, M. et al., "Survival of primary human hepatocytes and death of induced pluripotent stem cells in media lacking glucose and arginine," PLoS One, 2013, Vol. 8, e71897), the iPS cells were induced to differentiate to hepatocytes in 3 days when cultured in HSM, whereas the iPS cells died.

There is a report that the iPS cells undergo apoptosis when cultured in HSM (Tomizawa, M. et al., "Survival of primary human hepatocytes and death of induced pluripotent stem cells in media lacking glucose and arginine," PLoS One, 2013, Vol. 8, e71897). In view of the foregoing, reagents for enhancing the survival of the iPS cells through apoptosis inhibition were searched for. Specifically, M50054, a CTP inhibitor, and a DAPK inhibitor at various concentrations were added in the culture of iPS cells in HSM, and the cells were observed with an optical microscope after 3 days.

Figure 2:
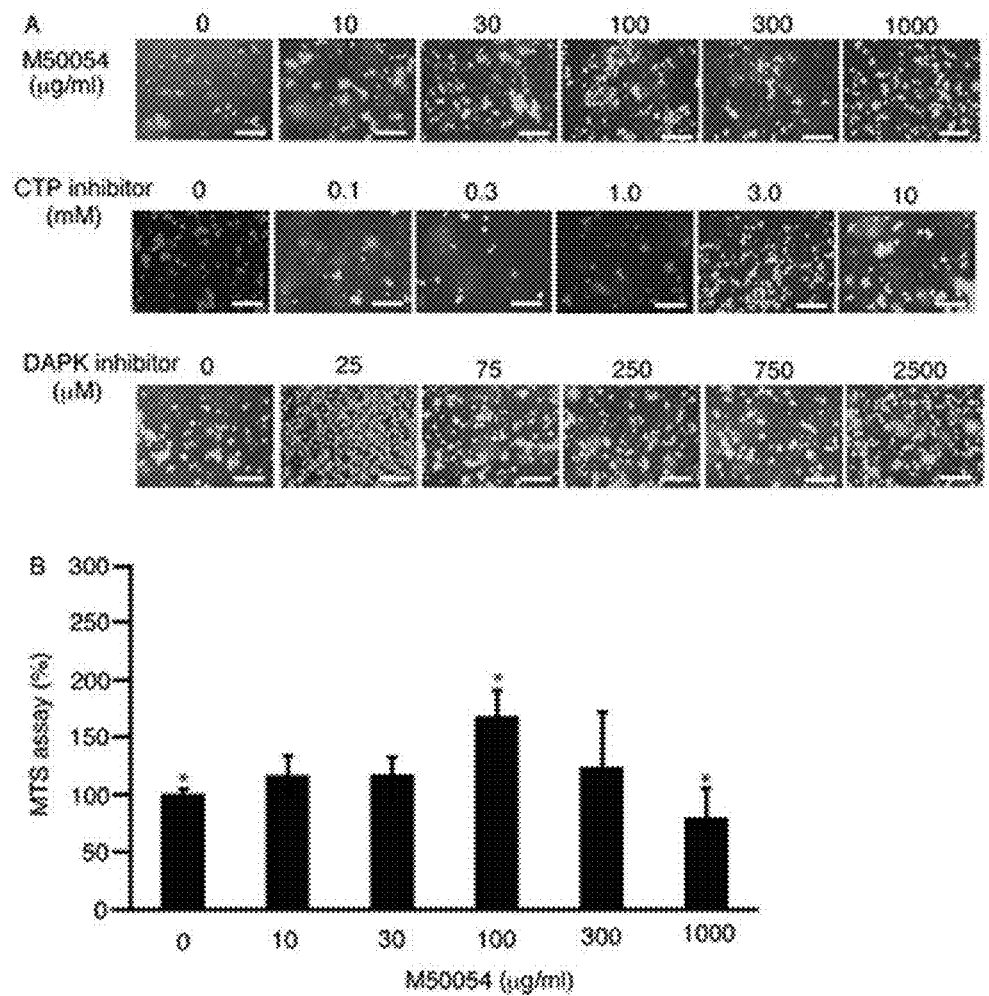
FIG. 2 shows a result of searching for a chemical substance that inhibit the apoptosis of a human iPS cell line (201B7) during culture. An apoptosis inhibitor M50054 exhibited a suppressing effect on the apoptosis of the human iPS cell line. The panel A describes that M50054 exhibited a higher suppressing effect on the apoptosis of the human iPS cell line in comparison to a CTP inhibitor or a DAPK inhibitor. The CTP inhibitor is an inhibitor of mitochondrial citrate transport protein. The DAPK inhibitor is an inhibitor of death-associated protein kinase. The original magnification is 100× and the scale bar is 50 μm. The panel B describes that M50054 exhibited the highest apoptosis inhibitory effect at a concentration of 100 μg/mL. Surviving cells were measured by MTS assay. The ordinate axis indicates a ratio (%) of the number of surviving cells in culture with addition of M50054 to the number of surviving cells in culture without addition of M50054. "*" indicates that a significant difference (P<0.05) was found in statistical analysis using one-way analysis of variance (JMP10.0.2; SAS Institute) (Example 1).

As shown in the panel A of FIG. 2, among the investigated reagents, the iPS cells died in the culture with addition of each of the CTP inhibitor and the DAPK inhibitor, whereas some of the iPS cells survived in the culture with addition of M50054 at a concentration of 100 μg/mL.

In view of the foregoing, MTS assay was performed 48 hours after the addition of M50054. As a result, as shown in the panel B of FIG. 2, the maximum absorbance was found in the culture with addition of M50054 at a concentration of 100 g/mL. Statistical analysis using one-way analysis of variance (JMP10.0.2; SAS Institute) showed that M50054 exhibited a significantly high value (P<0.05) at 100 μg/mL as compared to 0 μg/mL and 1,000 μg/mL. This suggested that M50054 showed cell toxicity at 1,000 μg/mL.

There is a report that NEAA and sodium pyruvate have a preferable effect on the survival of mouse ES cells (Abe, K. et al., "Endoderm-specific gene expression in embryonic stem cells differentiated to embryoid bodies," Experimental Cell Research, 1996, Vol. 229, No. 1, p. 27-34). The pluripotent stem cells have an immature citric acid cycle and hence obtain energy mainly from glycolysis. That is, in order for the pluripotent stem cells to survive, a large amount of glucose is required, and hence sodium pyruvate, which is a product of glycolysis, is required. In addition, various amino acid metabolism pathways are also immature, and hence the addition of NEAA is desired for the culture of the pluripotent stem cells.

On the other hand, HSM is a medium developed for the purpose of killing undifferentiated iPS cells to select hepatocytes when differentiation of iPS cells to hepatocytes is performed. Then, HSM was not added with NEAA and sodium pyruvate (Tomizawa, M. et al., "Survival of primary human hepatocytes and death of induced pluripotent stem cells in media lacking glucose and arginine," PLoS One, 2013, Vol. 8, e71897).

In this Example, the addition of NEAA and sodium pyruvate (1 mM) to HSM was investigated for the purpose of enhancing the survival of iPS cells. Specifically, iPS cells were cultured for 2 days in a medium prepared by adding NEAA and sodium pyruvate (1 mM) to HSM, and the expression of AFP gene was measured by real-time quantitative PCR. In addition, iPS cells were cultured for 48 hours in a medium prepared by adding M50054 at 100 g/mL to HSM, and the expression of AFP gene was measured by real-time quantitative PCR.

Figure 3:
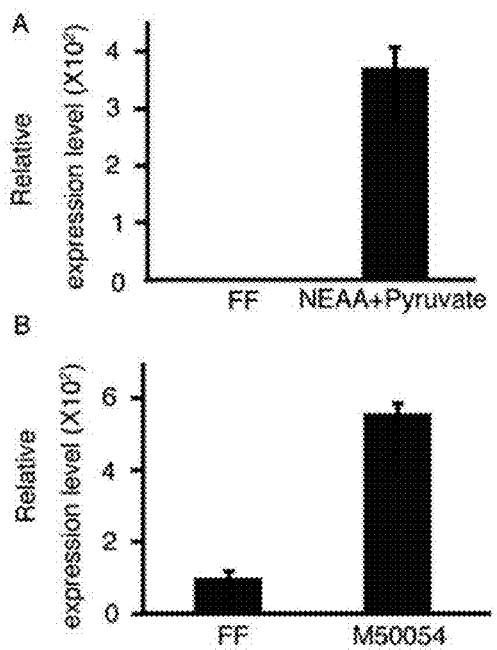
FIG. 3 shows that non-essential amino acids (sometimes abbreviated as NEAA) and sodium pyruvate having an effect on the survival of mouse ES cells exhibited an effect on the survival of culture cells obtained by culturing a human iPS cell line (201B7) in HSM. The panel A shows the result of culture in a medium prepared by adding NEAA and sodium pyruvate to HSM. The panel B shows the result of culture in a medium prepared by adding M50054 to HSM. The ordinate axis indicates a relative expression level of AFP.

As shown in the panel A of FIG. 3, when the iPS cells were cultured for 2 days in the medium prepared by adding NEAA and sodium pyruvate (1 mM) to HSM, the expression of AFP gene was found to be upregulated in the cultured cells. In addition, as shown in the panel B of FIG. 3, when the iPS cells were cultured for 48 hours in the medium prepared by adding M50054 at 100 g/mL to HSM, the expression of AFP gene was found to be upregulated in the cultured cells.

Next, growth factors for promoting differentiation of iPS cells to hepatocytes were searched for. Specifically, iPS cells were cultured for 1 week in iPSm(-) supplemented with various growth factors. After that, RNA was extracted and the expression level of AFP gene was analyzed by real-time quantitative PCR.

Figure 4:
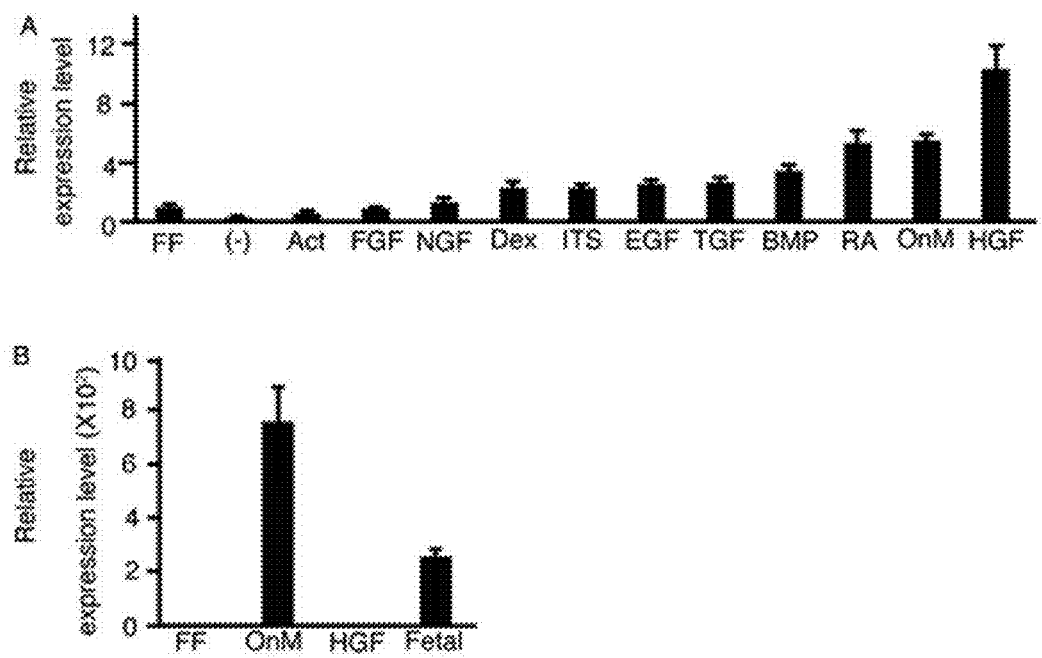
FIG. 4 shows the results of search for growth factors that promote differentiation of a human iPS cell line (201B7) into hepatocytes. The panel A shows the relative expression levels of AFP in cultured cells after 1 week of culture of iPS cells in media supplemented with various growth factors.

As shown in the panel A of FIG. 4, among the investigated growth factors, oncostatin M and HGF each exhibited an upregulating effect on the expression of AFP gene in the cells obtained by culturing the iPS cells.

In vies of the foregoing, iPS cells were cultured for 48 hours in HSM supplemented with each of oncostatin M and HGF alone. After that, RNA was extracted and the expression level of AFP gene was detected by real-time quantitative PCR. As shown in the panel B of FIG. 4, oncostatin M exhibited a high upregulating effect on the expression of AFP gene as compared to HGF. The expression of AFP gene in the cells cultured in the medium supplemented with oncostatin M was more upregulated than the expression of the gene in fetal liver. A possible reason why oncostatin M exhibited a higher upregulating effect on the expression of AFP gene than HGF, which was unlike the results shown in the panel A of FIG. 4, is that there are differences in experimental conditions, such as a period of time for culture and a medium, between the results shown in the panel A of FIG. 4 and the results shown in the panel B of FIG. 4.

FPH1 and FH1 are each a low-molecular-weight compound for promoting differentiation of iPS cells to hepatocytes (Shan, J. et al., "Identification of small molecules for human hepatocyte expansion and iPS differentiation," Nature Chemical Biology, 2013, Vol. 9, No. 8, p. 514-520): In view of the foregoing, differentiation of iPS cells to hepatocytes was investigated through the use of a medium prepared by adding each of FPH1 and FH1 to HSM. Specifically, iPS cells were cultured for 2 days in a medium prepared by adding each of FPH1 (10 μM) and FH1 (10 μM) alone or a combination thereof to HSM. After that, RNA was extracted and the expression level of AFP gene was analyzed by real-time quantitative PCR. Thus, a condition under which expression level of AFP becomes high was investigated.

Figure 5:
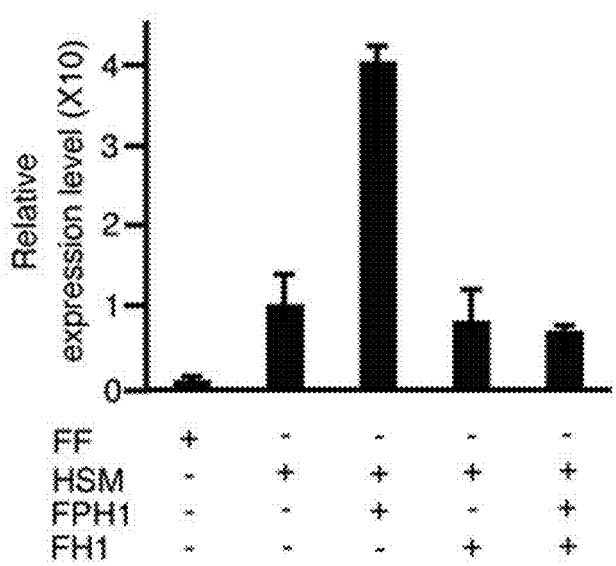
FIG. 5 shows that hepatocyte functional proliferation inducer (hereinafter abbreviated as FPH1), a low-molecular-weight compound for promoting differentiation to hepatocytes, upregulated the relative expression level of AFP in a human iPS cell line (201B7) cultured in HSM. On the other hand, hepatocyte functional enhancer 1 (hereinafter abbreviated as FH1) did not exhibit such effect.

As shown in FIG. 5, it was revealed that when the cells were cultured in the medium prepared by adding FPH1 alone to HSM, the expression level of AFP gene in the cultured cells was increased.

HDI was prepared in consideration of the condition that was revealed from the above-mentioned results. Then, iPS cells were cultured in HDI for 2 days and then observed for morphology with an optical microscope. Further, RNA was extracted and the expression levels of various genes were analyzed by real-time quantitative PCR.

Figure 6:
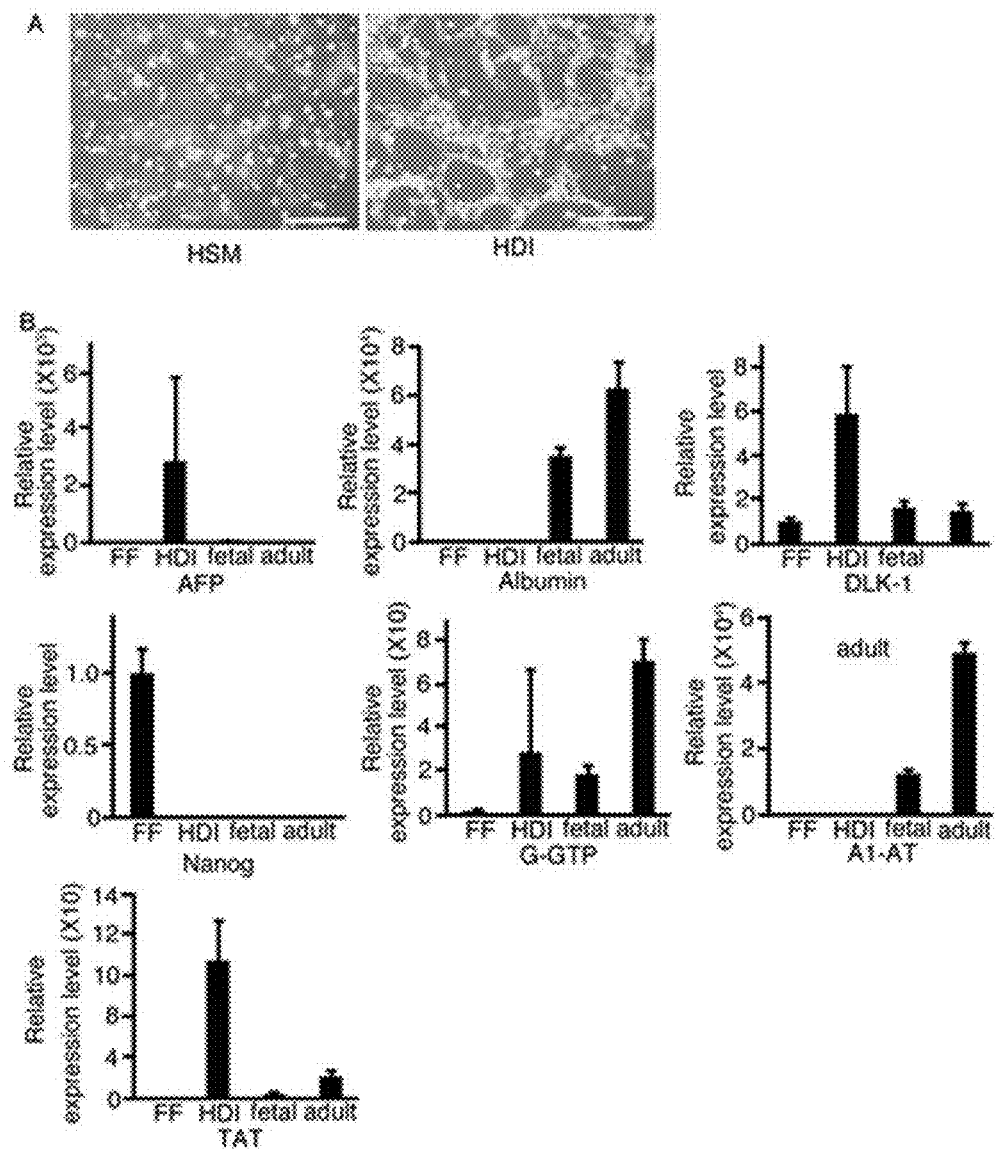
FIG. 6 shows the morphology of cultured cells and the relative expression levels of various genes after 2 days of culture of a human iPS cell line (201B7) in a culture medium (hereinafter referred to as hepatocyte differentiation inducer, which is sometimes abbreviated as HDI) prepared by adding oncostatin M, FPH1, M50054, NEAA, sodium pyruvate, nicotinamide, and L-glutamine to HSM. The cell morphology observed with an optical microscope is shown in the panel A. The original magnification is 100×. The relative expression levels of various genes are shown in the panel B.

As shown in the panel A of FIG. 6, a large number of cells survived in the culture in HDI as compared to the culture in HSM.

In addition, as shown in the panel B of FIG. 6, it was revealed that when the cells were cultured in HDI, the expression of AFP was upregulated and the expression of γ-glutamyl transpeptidase (hereinafter abbreviated as G-GTP), a marker of bile duct epithelial cells, was also upregulated similarly to fetal liver. As described above, the cells cultured in HDI expressed both markers of hepatocytes and bile duct epithelial cells, suggesting that the cells were similar to hepatoblasts (that are undifferentiated hepatocytes having an ability to differentiate to hepatocytes and bile duct epithelial cells). In addition, the absence of the expression of albumin suggested that the cells cultured in HDI were still hepatoblasts at a more undifferentiated stage than hepatocytes. Further, the expression of DLK-1, a marker of hepatoblasts, was upregulated in the cells cultured in HDI. This supported that the cells were similar to hepatoblasts. On the other hand, the expression of Nanog, which was specifically expressed in pluripotent stem cells and early embryo, almost disappeared in the cells cultured in HDI, suggesting that the cells had lost pluripotency.

Figure 7:
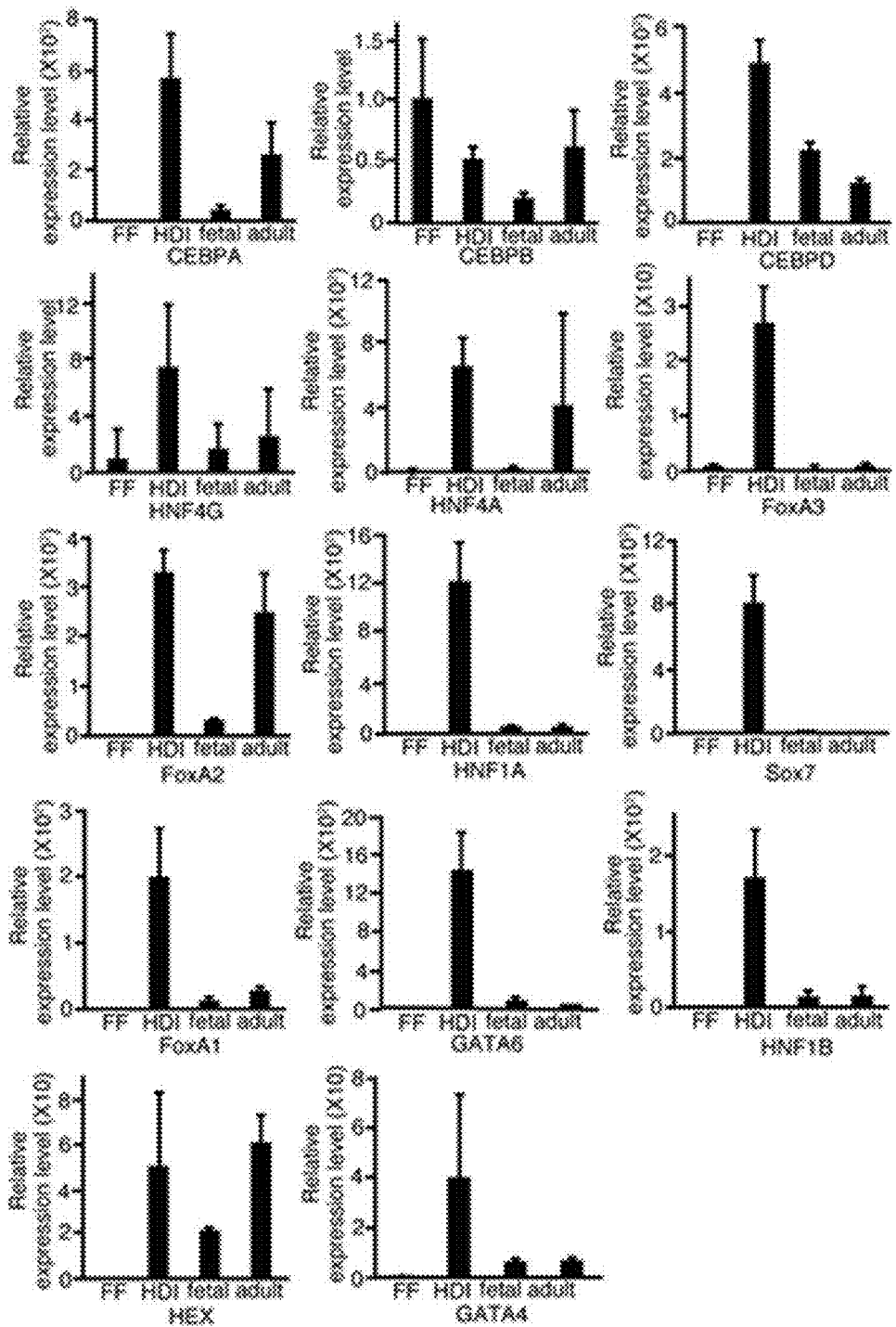
FIG. 7 shows the relative expression levels of various genes in cultured cells after 2 days of culture of a human iPS cell line (201B7) in HDI.

Further, as shown in FIG. 7, the expression levels of hepatocyte-specific transcription factors were found to be upregulated in the cells after the culture of the iPS cells in HDI. The expression levels of hepatocyte-specific transcription factors CEBPA, CEBPB, CEBPD, HNF4G, HNF4A, FoxA3, FoxA2, HNF1A, Sox7, FoxA1, GATA6, HNF1B, HEX, and GATA4 were found to be upregulated. The above-mentioned results suggested that after the iPS cells had been cultured in HDI, the expression levels of the hepatocyte-specific transcription factors were upregulated in the cultured cells.

Figure 8:
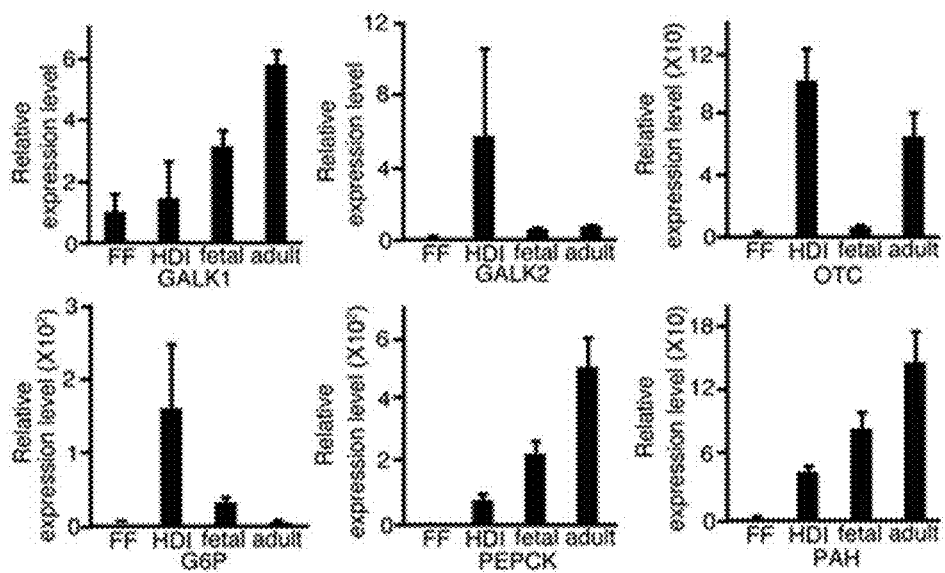
FIG. 8 shows that the relative expression levels of galactokinase 2 (GALK2), which is involved in galactose metabolism, and ornithine transcarbamylase (OTC), which is involved in the urea cycle, were upregulated in cultured cells after 2 days of culture of a human iPS cell line (201B7) in HDI. The expression of glucose-6-phosphatase (G6P), which is involved in glucose metabolism, was also upregulated. On the other hand, the expression levels of phosphoenolpyruvate carboxykinase (PEPCK) and phenylalanine hydroxylase (PAH) were upregulated to levels comparable to those in fetal liver, but did not reach their levels in adult liver (Example 1).

In addition, the expressions of metabolism enzymes were investigated. As a result, as shown in FIG. 8, the expressions of GALK2, an enzyme involved in galactose metabolism, and OTC, an enzyme involved in the urea cycle, were upregulated. In addition, the expression of G6P, an enzyme involved in glucose metabolism, was also upregulated. On the other hand, the expression levels of phosphoenolpyruvate carboxykinase (PEPCK) and phenylalanine hydroxylase (PAH) were upregulated to levels comparable to those in fetal liver, but did not reach their levels in adult liver. The above-mentioned results suggested that after the iPS cells had been cultured in HDI, galactose metabolism and ornithine metabolism were upregulated in the cultured cells. As described above, it was considered that such cultured cells were induced to differentiate to hepatocytes, but their differentiation state still remained at an undifferentiated stage.

Next, the expressions of CYP3A4, an enzyme involved in drug metabolism, and ALDH2, an enzyme involved in alcohol metabolism, were investigated.

Figure 9:
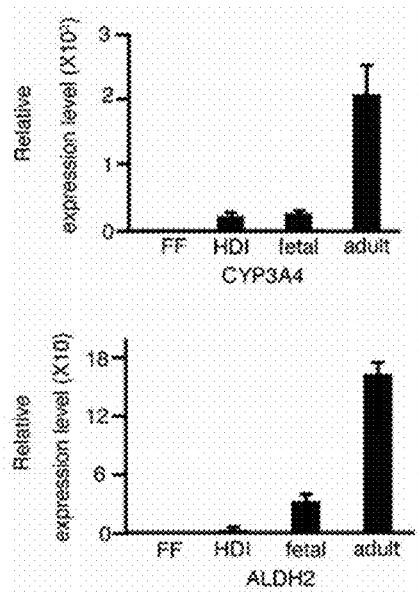
FIG. 9 shows that the relative expression levels of cytochrome P-450 nifedipine oxidase (CYP3A4), which is involved in drug metabolism, were upregulated in cultured cells after 2 days of culture of a human iPS cell line (201B7) in HDI to levels comparable to those in fetal liver. On the other hand, the expression level of aldehyde dehydrogenase 2 (ALDH2), which is involved in alcohol metabolism, was insufficient (Example'1).

As shown in FIG. 9, the expression of CYP3A4 was upregulated to a level comparable to that in fetal liver, but the expression level of ALDH2 was insufficient. The results indicated that after the iPS cells had been cultured in HDI, a part of metabolism-related functions of hepatocytes in the cultured cells was enhanced, but their differentiation state to hepatocytes remained at an undifferentiated stage.

As described above, when the iPS cells were cultured for 2 days in HDI having a composition shown in Table 1, the expressions of AFP, DLK-1, and G-GTP, markers of hepatoblasts, in the cultured cells were found to be comparable to those in fetal liver. On the other hand, the expression of albumin, a marker of mature hepatocytes, was not found. Accordingly, the cells obtained by culturing the iPS cells in HDI can be considered to be hepatoblasts. It was revealed that the expressions of CYP3A4, which is involved in drug metabolism, and ALDH2, which is related to alcohol metabolism, were also increased to levels comparable to those in fetal liver. Accordingly, it is expected that the hepatoblasts obtained by such culture may be used for in vitro tests on a drug metabolism function and an alcohol metabolism function of hepatocytes. On the other hand, the expression of Nanog in such cultured cells was reduced to a level comparable to that in fetal liver, suggesting that the cells had lost pluripotency. Accordingly, the hepatoblasts obtained by such culture are considered to have an extremely low risk of forming a tumor when transplanted for liver disease treatment, and hence are highly useful.

Example 2

As shown in Example 1, it was revealed that when the iPS cells were cultured in HDI having a composition shown in Table 1, hepatoblasts were induced to differentiate in a short period of time. In a method of inducing differentiation to hepatocyte-lineage cells using HDI, a condition for obtaining a larger number of hepatocyte-lineage cells, and a condition for inducing differentiation to more mature hepatocytes were investigated.

Specifically, a culture condition was conducted, which comprised culturing iPS cells in a culture medium other than HDI, and then further culturing the cells in HDI after changing the culture media to HDI.

1. Test Media

The following media were used as the culture media other than HDI, and the investigations were carried out.

(1) ReproFF (product number: RCHEMD004, manufactured by ReproCELL Incorporated)
(2) Leibovitz's-15 (product number: 11415, manufactured by Life Technologies)
(3) Dulbecco's Modified Eagle Medium (product number: D5796, manufactured by Sigma-Aldrich)
(4) Roswell Park Memorial Institute-1640 (product number: R8758, manufactured by Sigma-Aldrich)
(5) William's E medium (manufactured by Life Technologies)
(6) Dulbecco's Modified Eagle Medium: Nutrient Mixture F-12 (product number: 11330-032, manufactured by Life Technologies)
(7) Minimum Essential Medium (product number: 11090-081, manufactured by Life Technologies)
(8) Glasgow Minimum Essential Medium (product number: 11710-035, manufactured by Life Technologies)
(9) Improved Minimum Essential Medium (product number: 10373-017, manufactured by Life Technologies)
(10) Iscove's Modified Dulbecco's Medium (product number: 12440-053, manufactured by Life Technologies)
(11) Connaught Medical Research Laboratories Medium 1066 (product number: 11530-037, manufactured by Life Technologies)
(12) Basal Medium Eagle (product number: 21010-046, manufactured by Life Technologies)
(13) McCoy's 5A Medium (product number: 16600-082, manufactured by Life Technologies)
(14) MCDB 131 Medium (product number: 10372-019, manufactured by Life Technologies)

2. Cell Culture

201B7 cells were seeded to a 6-well plate coated with Matrigel (manufactured by Asahi Glass Co., Ltd.) based on the method described in Example 1. ReproFF was used as a cell culture medium, and the cells were cultured in a 5% $CO_2$ incubator at 37° C. After the cells had reached 70% confluence, the cells were cultured for 7 days in a test medium supplemented with 10% KSR, 0.03 mg/mL proline, and 1.2 mg/mL nicotinamide. After 7 days of the culture in the test medium, the cells were further cultured for 2 days in HDI in exchange for the test medium.

3. Measurement of Expression Level of AFP

Cell differentiation was confirmed by measuring the expression of AFP gene by real-time quantitative PCR. RNA extraction, cDNA synthesis, and real-time quantitative PCR were performed by the same methods as the methods described in Example 1. Human fetal liver-derived total RNA (manufactured by Clontech) was used as a control.

4. Results

First, selection of a culture medium for use in the culture of the 201B7 cells before culturing the cells in HDI (hereinafter sometimes referred to as preculture) was carried out. The selection of culture medium was conducted by culturing the 201B7 cells in various test media, measuring the expression levels of AFP in the resultant cells, and assessing that a culture medium bringing an increase in the expression level of AFP was a culture medium capable of initiating the induction of differentiation of 201B7 cells to hepatocyte-lineage cells.

Figure 10:
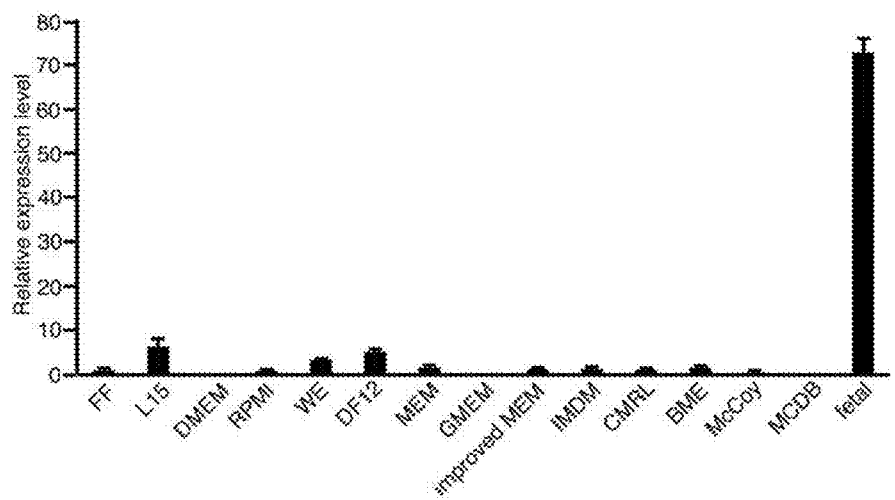
FIG. 10 shows the expression levels of AFP in cell cultures obtained by culturing a human iPS cell line (201B7) in 14 kinds of culture media for 7 days. The ordinate axis of FIG. 10 indicates a relative expression level. Human fetal liver-derived RNA was used as a control for the expression level of AFP in cells. Abbreviations in FIG. 10 are described below. FF: ReproFF, L15: Leibovitz's-15, DMEM: Dulbecco's Modified Eagle Medium, RPMI: Roswell Park Memorial Institute-1640, WE: William's E medium, DF12: Dulbecco's Modified Eagle Medium: Nutrient Mixture F-12, MEM: Minimum Essential Medium, GMEM: Glasgow Minimum Essential Medium, improved MEM: improved Minimum Essential Medium, IMDM: Iscove's Modified Dulbecco's Medium, CMRL: Medium 1066: Connaught Medical Research Laboratories Medium 1066, BME: Basal Medium Eagle, McCoy: McCoy's 5A, MCDB: MCDB131, fetal: human fetal liver (Example 2).

As shown in FIG. 10, it was revealed that the expression level of AFP in the cells was high in the culture in three kinds of culture media, i.e., Leibovitz's-15 (hereinafter sometimes abbreviated as L15), William's E medium (hereinafter sometimes abbreviated as WE), and Dulbecco's Modified Eagle Medium: Nutrient Mixture F-12 (hereinafter sometimes abbreviated as DF12) among the investigated 14 kinds of test media, as compared to the culture in each of the other test media. This suggested that those three kinds of culture media each served as a medium suitable for differentiation of 201B7 cells to hepatocyte-lineage cells.

Next, the 201B7 cells were precultured for 7 days in each of the selected three kinds of culture media, and then were cultured for 2 days in HDI in exchange for the culture media. The resultant cells were observed under an optical microscope. In addition, the expression level of AFP in the resultant cells was measured.

When the 201B7 cells are cultured in HDI from the start of the culture, cells having pluripotency, such as pluripotent stem cells, die, and only hepatocyte-lineage cells, such as hepatoblasts, survive, as illustrated in Example 1 and FIG. 6. In addition, when the 201B7 cells are cultured in ReproFF and then cultured in HDI, a remarkable decrease in the cell number is found.

Figure 11:
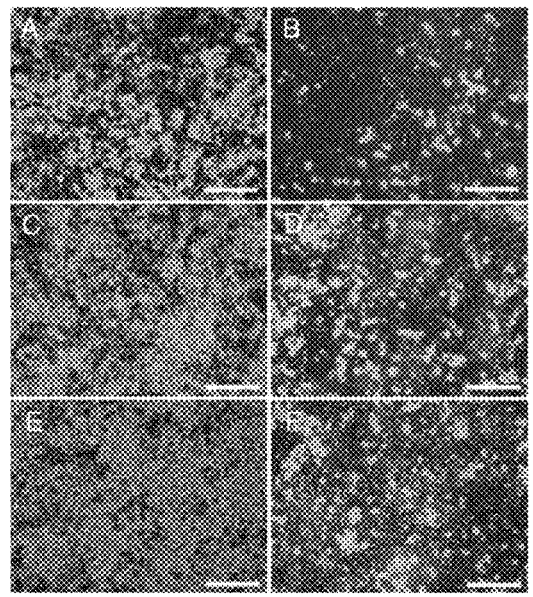
FIG. 11 shows the results of optical microscopic observation of cells obtained by culturing a human iPS cell line (201B7) in culture media Leibovitz's-15, William's E medium, and Dulbecco's Modified Eagle Medium: Nutrient Mixture F-12 for 7 days (panel A, panel C, and panel E, respectively), and cells obtained by culturing the cells in the culture media for 7 days and further culturing the cells in HDI for 2 days after changing the culture media to HDI (panel B, panel D, and panel F, respectively). The original magnification is 200× and the scale bar is 25 μm (Example 2).

On the other hand, when the cells cultured in L15, WE, and DF12 for 7 days (panels A, C, and E of FIG. 11, respectively) were further cultured in HDI for 2 days (panels B, D, and F of FIG. 11, respectively), the cells did not die and a large number of cells were found to survive. Accordingly, it was confirmed that the induction of differentiation to hepatocyte-lineage cells was initiated in the 201B7 cells cultured in L15, WE, and DF12.

Figure 12:
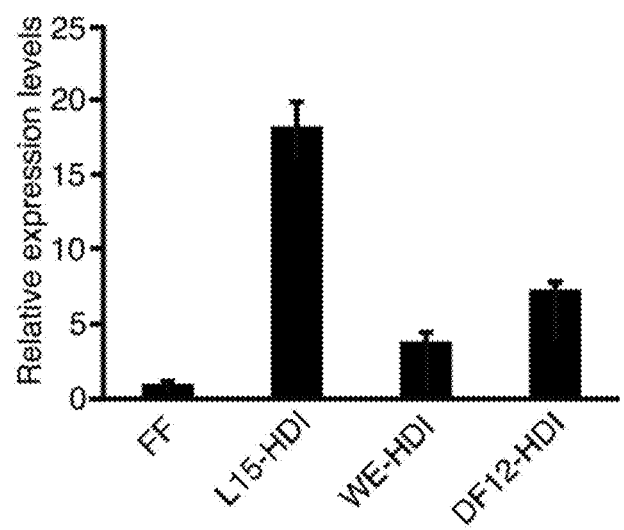
FIG. 12 shows that the expression level of AFP was remarkably increased in cells obtained by culturing a human iPS cell line (201B7) in culture media Leibovitz's-15, William's E medium, and Dulbecco's Modified Eagle Medium: Nutrient Mixture F-12 for 7 days and then further culturing in HDI for 2 days after changing the culture media to HDI, as compared to cells cultured in ReproFF. Abbreviations in FIG. 12 are described below. FF: cells cultured in ReproFF, L15-HDI: cells cultured in Leibovitz's-15 and then cultured in HDI after changing the culture medium, WE-HDI: cells cultured in William's E medium and then cultured in HDI after changing the culture medium, DF12-HDI: cells cultured in Dulbecco's Modified Eagle Medium: Nutrient Mixture F-12 and then cultured in HDI after changing the culture medium (Example 2).

In addition, as shown in FIG. 12, it was revealed that the expression level of AFP was remarkably increased in the cells cultured in L15, WE, and DF12 for 7 days and then further cultured in HDI for 2 days as compared to the cells cultured in ReproFF and the cells cultured in each of L15, WE, and DF12 alone for 7 days (see FIG. 10). The expression of AFP was remarkable in the cells that were precultured in L15 among the three kinds of media and further cultured in HDI for 2 days. The results also confirmed that the induction of differentiation to hepatocyte-lineage cells was initiated in the 201B7 cells cultured in L15, WE, and DF12.

The above-mentioned results confirmed that when human iPS cells were cultured in a culture medium other than HDI to initiate the induction of differentiation to hepatocyte-lineage cells, and then were further cultured in HDI in exchange for the culture medium, a cell survival rate was increased as compared to the human iPS cells cultured in HDI from the start of the culture, and the expression level of AFP in the resultant cells was upregulated. In addition, hepatocyte-lineage cells, such as hepatoblasts, obtained by such culture method are obtained in a large amount as compared to a method of culturing human iPS cells in HDI from the start of the culture. Accordingly, such culture condition is expected to be applicable to a method comprising inducing differentiation of human iPS cells to hepatocyte-lineage cells and then completing differentiation to mature hepatocytes.

According to the present invention, hepatoblasts can be obtained by culturing pluripotent stem cells, such as iPS cells, for a short period of time.

The present invention is extremely useful in the field of drug development and the field of regenerative medicine.

What is claimed is:

1. A method of producing hepatoblasts from pluripotent stem cells, comprising culturing pluripotent stem cells in a culture medium having a composition shown in Table 1 below:

TABLE 1

| Hepatocyte differentiation inducer (HDI) (1 L) | inorganic salts | |
|---|---|---|
| | $CaCl_2 \cdot 2H_2O$ | 0.185 g |
| | $MgCl_2 \cdot 6H_2O$ | 0.203 g |
| | $MgSO_4$(anhyd) | 0.098 g |
| | KCl | 0.4 g |
| | $KH_2PO_4$ | 0.06 g |
| | NaCl | 7.915 g |
| | $Na_2HPO_4$ | 0.19 g |
| | amino acids | |
| | L-alanine | 0.225 g |
| | L-asparagine,$H_2O$ | 0.25 g |
| | L-cysteine | 0.12 g |
| | glycine | 0.2 g |
| | L-histidine,HCl,$H_2O$ | 0.25 g |
| | L-isoleucine | 0.25 g |
| | L-leucine | 0.125 g |

TABLE 1-continued

| | L-lysine,HCl | 0.075 g |
|---|---|---|
| | L-methionine | 0.075 g |
| | L-phenylalanine | 0.125 g |
| | L-serine | 0.2 g |
| | L-threonine | 0.3 g |
| | L-tryptophan | 0.02 g |
| | L-valine | 0.1 g |
| | Others | |
| | phenol red, Na | 0.01 g |
| | $NaHCO_3$ | 2.745 g |
| | MEM vitamin solution (100 X) | 10 ml |
| | serum replacement | 100 ml |
| | glutamine | 0.3 g |
| | ornithine | 0.169 g |
| | galactose | 0.9 g |
| | oncostatin M | 0.02 g |
| | Hepatocyte functional proliferation inducer (FPH1) | 3.88 g |
| | Apoptosis inhibitor M50054 | 100 mg |
| | non-essential amino acids, consisting of glycine, L-alanine, L-aspargine, L-aspartic acid, L-glutamic acid, L-proline and L-serine | 10 ml |

TABLE 1-continued

|  |  |  |
|---|---|---|
| sodium pyruvate | 10 | ml |
| nicotinamide | 1.2 | g |
| proline | 0.03 | g. |

2. The method of producing hepatoblasts from pluripotent stem cells according to claim 1, further comprising, before the culturing pluripotent stem cells in the culture medium having a composition shown in Table 1, culturing the pluripotent stem cells in any one culture medium selected from the group consisting of the following culture media:
(1) Leibovitz's-15;
(2) William's E medium; and
(3) Dulbecco's Modified Eagle Medium: Nutrient Mixture F-12.

3. The method of producing hepatoblasts from pluripotent stem cells according to claim 1, wherein the pluripotent stem cells are induced pluripotent stem cells.

4. The method of producing hepatoblasts from pluripotent stem cells according to claim 1, wherein the culturing pluripotent stem cells in a culture medium having the composition shown in Table 1 is culturing the pluripotent stem cells in the culture medium for at least 2 days.

5. The method of producing hepatoblasts from pluripotent stem cells according to claim 1, wherein the culturing pluripotent stem cells in a culture medium having the composition shown in Table 1 is culturing the pluripotent stem cells in the culture medium for 2 days.

6. A method of producing hepatoblasts from induced pluripotent stem cells (iPS cells), comprising culturing iPS cells in a culture medium having a composition shown in Table 1 below for 2 days:

TABLE 1

| Hepatocyte differentiation inducer (HDI) (1 L) | inorganic salts | |
|---|---|---|
| | CaCl$_2$,2H$_2$O | 0.185 g |
| | MgCl$_2$,6H$_2$O | 0.203 g |
| | MgSO$_4$(anhyd) | 0.098 g |
| | KCl | 0.4 g |
| | KH$_2$PO$_4$ | 0.06 g |
| | NaCl | 7.915 g |
| | Na$_2$HPO$_4$ | 0.19 g |
| | amino acids | |
| | L-alanine | 0.225 g |
| | L-asparagine,H$_2$O | 0.25 g |
| | L-cysteine | 0.12 g |
| | glycine | 0.2 g |
| | L-histidine,HCl,H$_2$O | 0.25 g |
| | L-isoleucine | 0.25 g |
| | L-leucine | 0.125 g |
| | L-lysine,HCl | 0.075 g |
| | L-methionine | 0.075 g |
| | L-phenylalanine | 0.125 g |
| | L-serine | 0.2 g |
| | L-threonine | 0.3 g |
| | L-tryptophan | 0.02 g |
| | L-valine | 0.1 g |
| | Others | |
| | phenol red, Na | 0.01 g |
| | NaHCO$_3$ | 2.745 g |
| | MEM vitamin solution (100 X) | 10 ml |
| | serum replacement | 100 ml |
| | glutamine | 0.3 g |
| | ornithine | 0.169 g |
| | galactose | 0.9 g |
| | oncostatin M | 0.02 g |

TABLE 1-continued

|  |  |  |
|---|---|---|
| Hepatocyte functional proliferation inducer (FPH1) | 3.88 | g |
| Apoptosis inhibitor M50054 | 100 | mg |
| non-essential amino acids, consisting of glycine, L-alanine, L-aspargine, L-aspartic acid, L-glutamic acid, L-proline and L-serine | 10 | ml |
| sodium pyruvate | 10 | ml |
| nicotinamide | 1.2 | g |
| proline | 0.03 | g. |

7. A method of producing hepatoblasts from induced pluripotent stem cells (iPS cells), comprising:
(A) culturing iPS cells in any one culture medium selected from the group consisting of the following culture media for 7 days:
(1) Leibovitz's-15;
(2) William's E medium; and
(3) Dulbecco's Modified Eagle Medium: Nutrient Mixture F-12; and
(B) culturing cells obtained in the step (A) in a culture medium having a composition shown in Table 1 below for 2 days:

TABLE 1

| Hepatocyte differentiation inducer (HDI) (1 L) | inorganic salts | |
|---|---|---|
| | CaCl$_2$,2H$_2$O | 0.185 g |
| | MgCl$_2$,6H$_2$O | 0.203 g |
| | MgSO$_4$(anhyd) | 0.098 g |
| | KCl | 0.4 g |
| | KH$_2$PO$_4$ | 0.06 g |
| | NaCl | 7.915 g |
| | Na$_2$HPO$_4$ | 0.19 g |
| | amino acids | |
| | L-alanine | 0.225 g |
| | L-asparagine,H$_2$O | 0.25 g |
| | L-cysteine | 0.12 g |
| | glycine | 0.2 g |
| | L-histidine,HCl,H$_2$O | 0.25 g |
| | L-isoleucine | 0.25 g |
| | L-leucine | 0.125 g |
| | L-lysine,HCl | 0.075 g |
| | L-methionine | 0.075 g |
| | L-phenylalanine | 0.125 g |
| | L-serine | 0.2 g |
| | L-threonine | 0.3 g |
| | L-tryptophan | 0.02 g |
| | L-valine | 0.1 g |
| | Others | |
| | phenol red, Na | 0.01 g |
| | NaHCO$_3$ | 2.745 g |
| | MEM vitamin solution (100 X) | 10 ml |
| | knockout serum replacement | 100 ml |
| | glutamine | 0.3 g |
| | ornithine | 0.169 g |
| | galactose | 0.9 g |
| | oncostatin M | 0.02 g |
| | Hepatocyte functional proliferation inducer (FPH1) | 3.88 g |
| | Apoptosis inhibitor M50054 | 100 mg |
| | non-essential amino acids, consisting of glycine, L-alanine, L-aspargine, L-aspartic acid, L-glutamic acid, L-proline and L-serine | 10 ml |
| | sodium pyruvate | 10 ml |
| | nicotinamide | 1.2 g |
| | proline | 0.03 g. |

\* \* \* \* \*

UNITED STATES PATENT AND TRADEMARK OFFICE
CERTIFICATE OF CORRECTION

PATENT NO.        : 10,006,005 B2
APPLICATION NO.   : 14/749715
DATED             : June 26, 2018
INVENTOR(S)       : Minoru Tomizawa Page 1 of 1

It is certified that error appears in the above-identified patent and that said Letters Patent is hereby corrected as shown below:

In the Claims

In Claim 1, in Table 1, Column 46, Line 64, "of glycine, L-alanine, L-aspargine," should read -- of glycine, L-alanine, L-asparagine --

In Claim 6, in Table 1, Column 48, Line 6, "of glycine, L-alanine, L-aspargine," should read -- of glycine, L-alanine, L-asparagine --

In Claim 7, in Table 1, Column 48, Line 50, "knockout serum replacement" should read -- serum replacement --

In Claim 7, in Table 1, Column 48, Line 57, "of glycine, L-alanine, L-aspargine," should read -- of glycine, L-alanine, L-asparagine --

Signed and Sealed this
Fourth Day of June, 2019

Andrei Iancu
*Director of the United States Patent and Trademark Office*